(12) United States Patent
Won et al.

(10) Patent No.: US 11,795,514 B2
(45) Date of Patent: Oct. 24, 2023

(54) ISOTHERMAL BASED-DUAL FUNCTIONAL OLIGONUCLEOTIDE INCLUDING REPORTER DYE, AND QUENCHER FOR ISOTHERMAL NUCLEIC ACID AMPLIFICATION AND MEASUREMENT METHODS USING

(71) Applicant: SD BIOSENSOR, INC., Suwon-si (KR)

(72) Inventors: Yoo Deok Won, Yongin-si (KR); Hae Joon Park, Seongnam-si (KR); Hyo Jin Seong, Yongin-si (KR); Mi Ae Lim, Yongin-si (KR); Sun Young Lee, Yongin-si (KR)

(73) Assignee: SD BIOSENSOR, INC., Suwon (KR)

( * ) Notice: Subject to any disclaimer, the term of this patent is extended or adjusted under 35 U.S.C. 154(b) by 343 days.

(21) Appl. No.: 15/779,616

(22) PCT Filed: Nov. 30, 2016

(86) PCT No.: PCT/KR2016/013944
§ 371 (c)(1),
(2) Date: May 29, 2018

(87) PCT Pub. No.: WO2017/095128
PCT Pub. Date: Jun. 8, 2017

(65) Prior Publication Data
US 2018/0346999 A1   Dec. 6, 2018

(51) Int. Cl.
*C12Q 1/6844* (2018.01)
*C12Q 1/70* (2006.01)

(52) U.S. Cl.
CPC ........... *C12Q 1/701* (2013.01); *C12Q 1/6844* (2013.01); *C12Q 1/70* (2013.01); *C12Q 2600/106* (2013.01); *C12Q 2600/112* (2013.01); *C12Q 2600/16* (2013.01)

(58) Field of Classification Search
CPC ................................ C12Q 1/68; C12Q 1/6884
See application file for complete search history.

(56) References Cited

U.S. PATENT DOCUMENTS

2017/0044631 A1* 2/2017 Nyan .................... C12Q 1/707

FOREIGN PATENT DOCUMENTS

| CN | 103045755 | 4/2013 |
| CN | 104962607 | 10/2015 |
| DE | 102011055247 | 5/2013 |
| WO | WO01/81631 | 11/2001 |
| WO | WO2010/048615 | 4/2010 |
| WO | WO2011/056933 | 5/2011 |
| WO | WO-2015063498 A2 * | 5/2015 ........... C12Q 1/6816 |

OTHER PUBLICATIONS

Chun, Dual priming oligonucleotide system for the multiplex detection of respiratory viruses and SNP genotyping of CYP2C19 gene, Nucleic Acids Research, 35(6):1-6, 2007. (Year: 2007).*
Biosearch Technologies, Labeling Oligos with Internal BHQ Dyes (Year: 2009).*
Benzine, Molecular Diagnostic Field Test for Point-of-Care Detection of Ebola Virus Directly From Blood, J Infect Dis, 214 (Suppl 3): S234-S242, Oct. 4, 2016. (Year: 2016).*
Di Fiori, The Effect of Dye-Dye Interactions on the Spatial Resolution of Single-Molecule FRET Measurements in Nucleic Acids, Biophysical Journal, 98(10): 2265-2272, 2010. (Year: 2010).*
Sigma, Sigma-Aldrich, Primers and Fluorescent Probes, 2014. (Year: 2014).*
Atdbio, FAM (fluorescein), HEX, JOE, ROX, TAMRA, TET, Texas Red and others, 2005-2021. (Year: 2021).*
J Ju et al., "Fluorescence energy transfer dye-labeled primers for DNA sequencing and analysis",Proc Natl Acad Sci USA, May 9, 1995; 92(10), pp. 4347-4351.
Nathan A. Tanner et al.; "Simultaneous multiple target detection in real-time loop-mediated isothermal amplification"; BioTechniques, vol. 53, Aug. 2012 (Aug. 1, 2012), pp. 81-89.
Xiong Ding et al.; "Mixed-Dye-Based Label-Free and Sensitive Dual Fluorescence for the Product Detection of Nucleic Acid Isothermal Multiple-Self-Matching-Initiated Amplification";Analytical Chemistry, vol. 87, No. 20, Oct. 20, 2015 (Oct. 20, 2015), pp. 10306-10314.
The extended European Search Report dated Mar. 11, 2019 with reference No. P124449EP00.

* cited by examiner

*Primary Examiner* — Samuel C Woolwine
*Assistant Examiner* — Carolyn L Greene
(74) *Attorney, Agent, or Firm* — Harvest IP Law, LLP

(57) ABSTRACT

The invention relates to an isothermal-based dual functional oligonucleotide containing quencher and reporter dye for an isothermal nucleic acid amplification and a method for nucleic acid amplification and measurement using the same. The present invention is directed to a method capable of obviating the need for an additional oligonucleotide, in addition to four to six types of oligonucleotides for a nucleic acid amplification reaction of LAMP, detecting the amount of fluorescence according to the amplification of the nucleic acid of target gene—specific sequence for DNA and RNA, enabling the detection also after the completion of the reaction, and detecting the amount of fluorescence in real-time. Therefore, the present invention allows simultaneous multiple tests by measuring the amount of fluorescence in one tube after the completion of the reaction or in real time while varying the reporter dye according to the target gene.

2 Claims, 17 Drawing Sheets
Specification includes a Sequence Listing.

[Fig. 1]
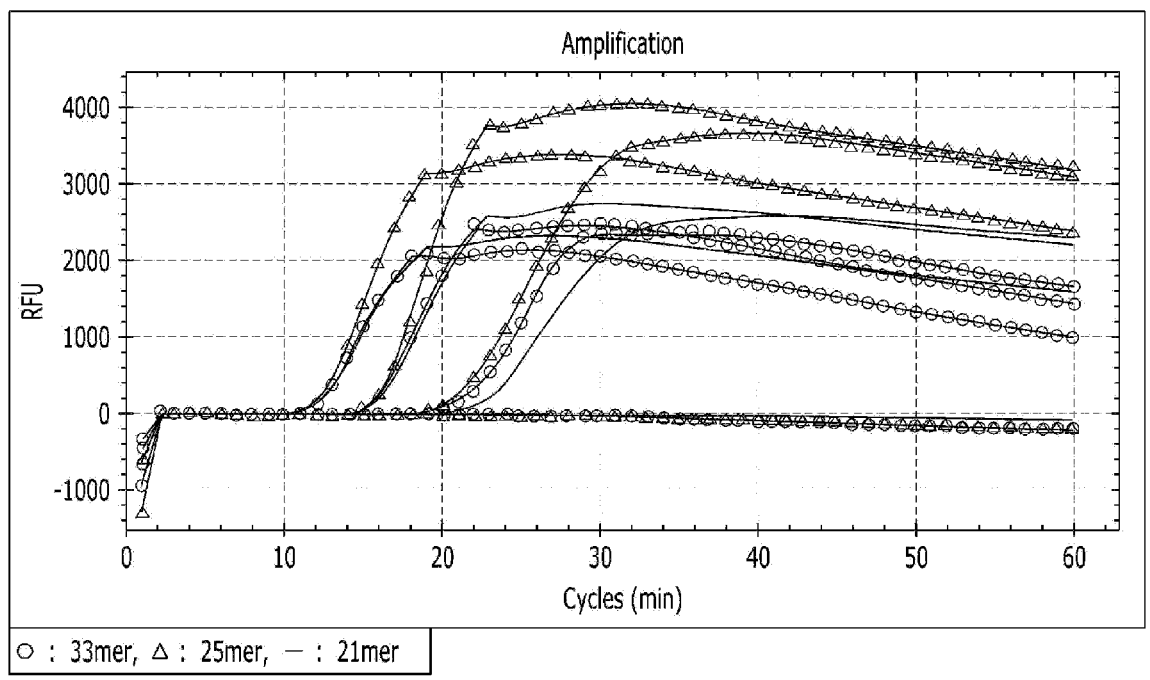

[Fig. 2]
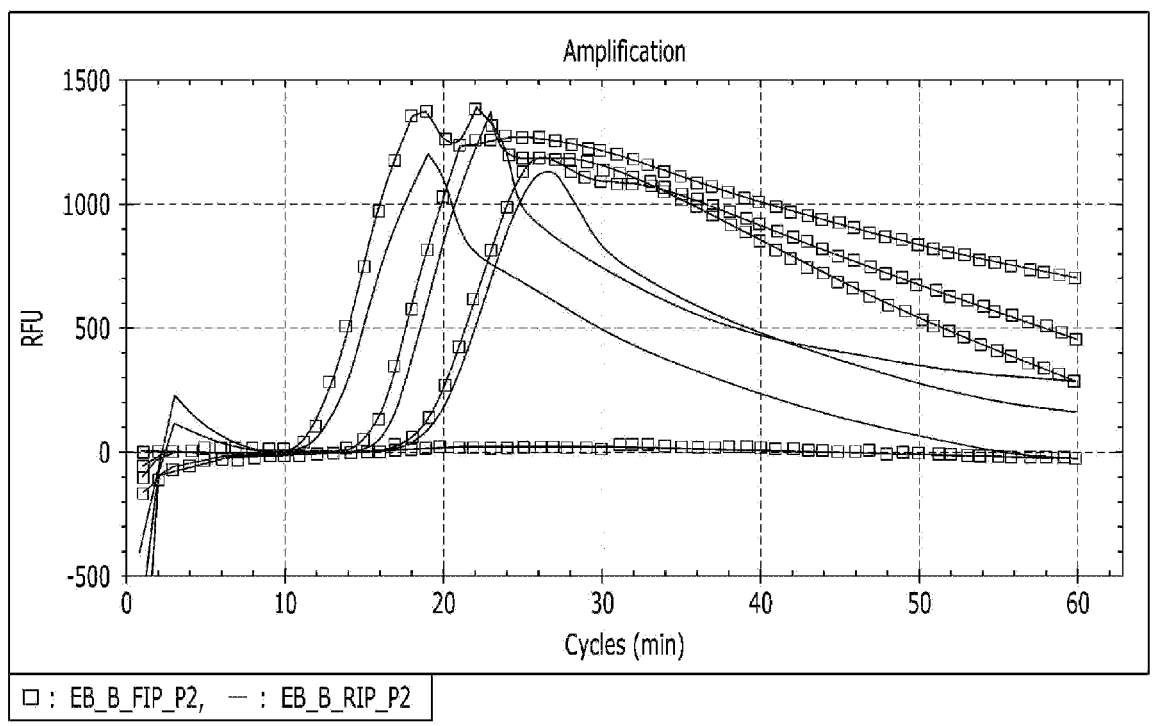

[Fig. 3]
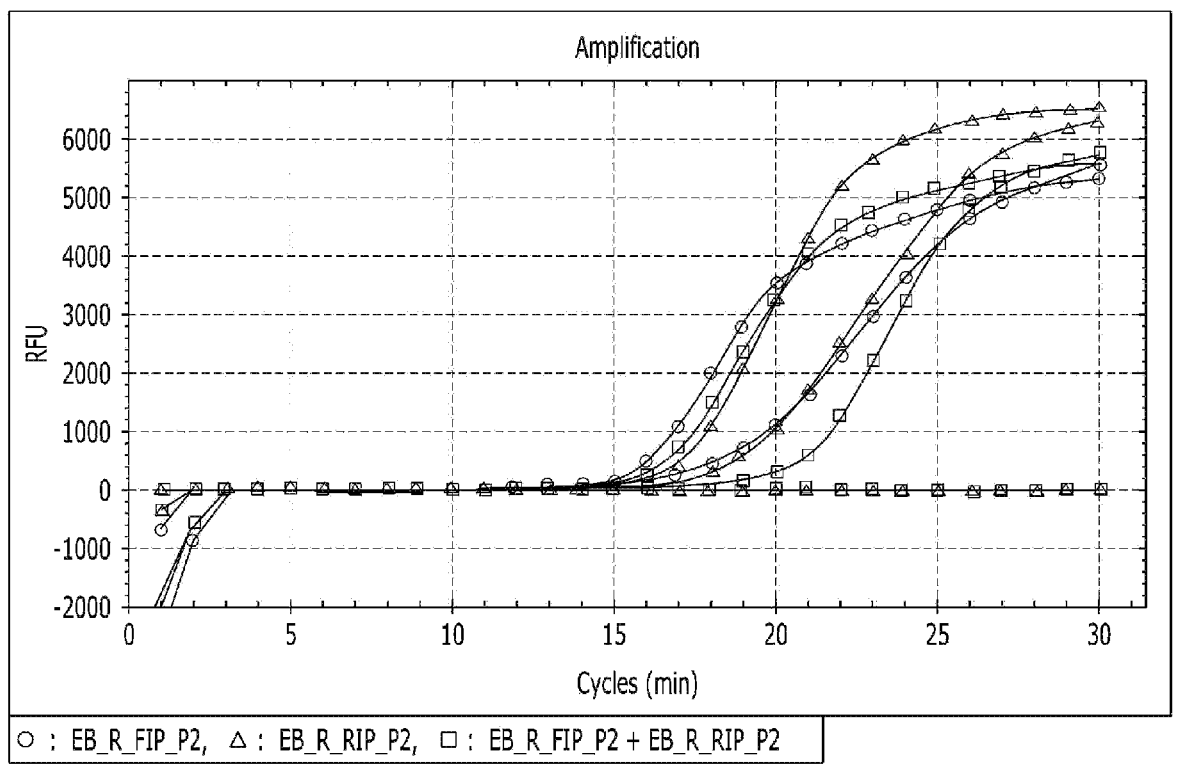

[Fig. 4]
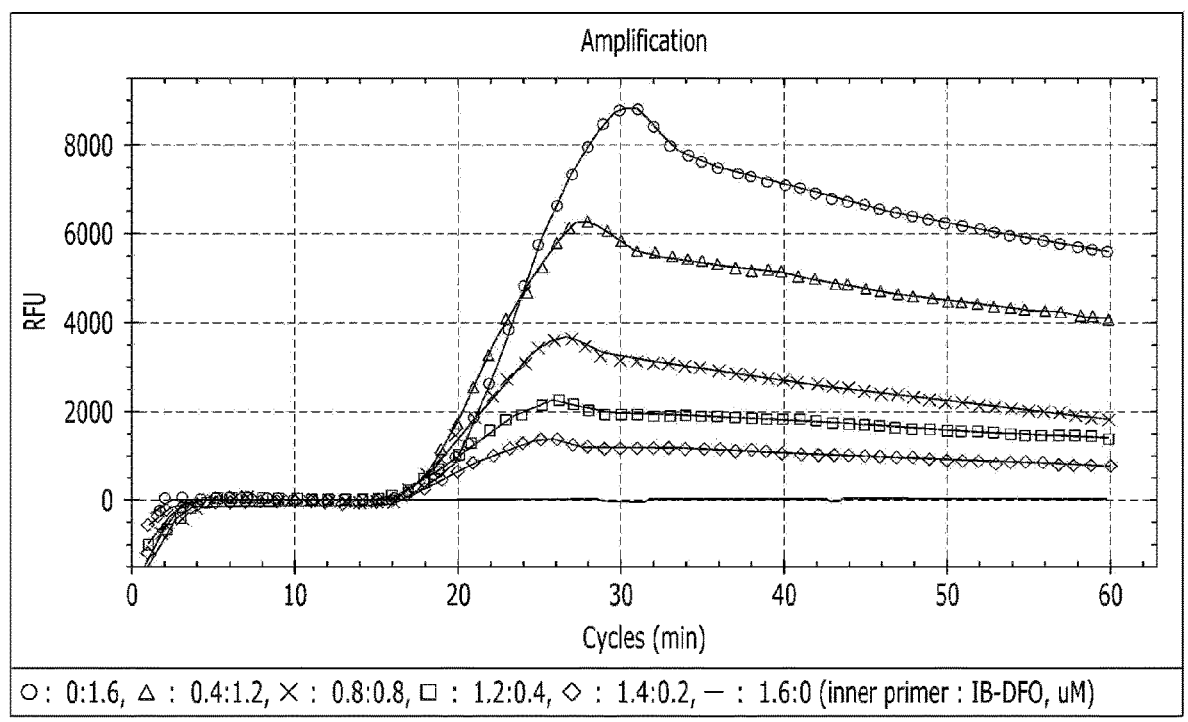

[Fig. 5]
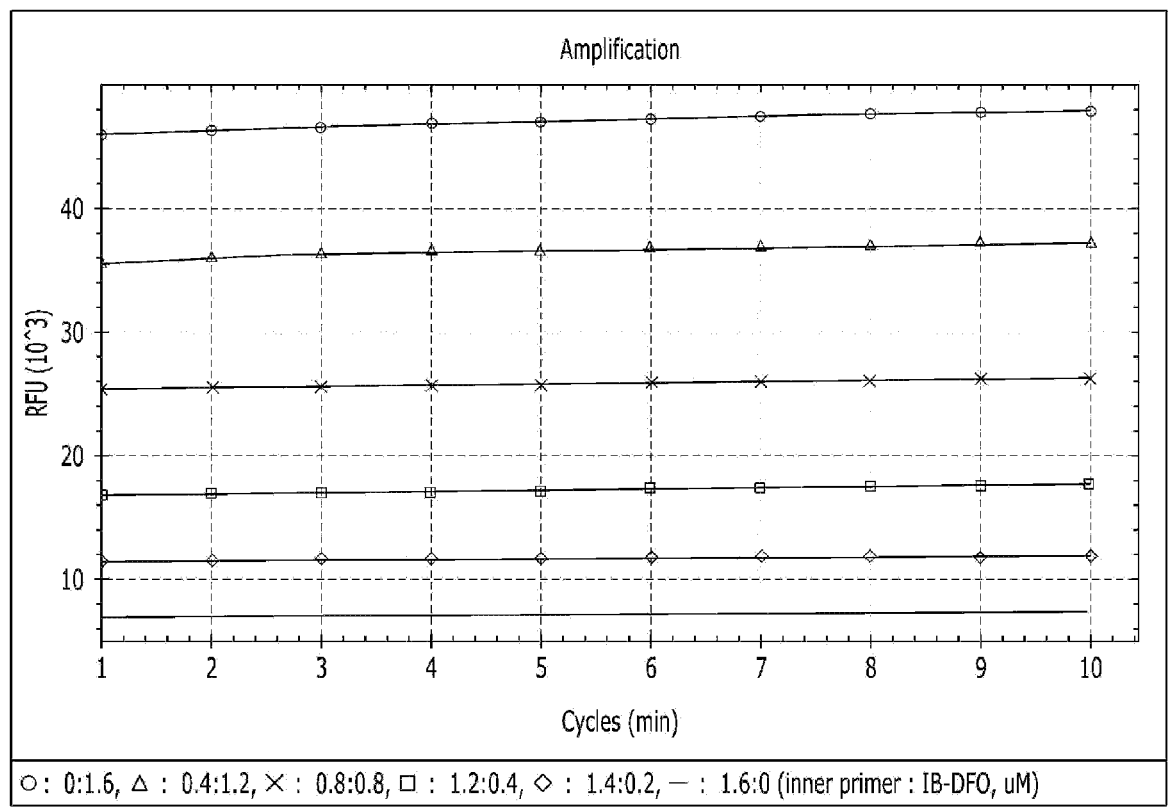

[Fig. 6]
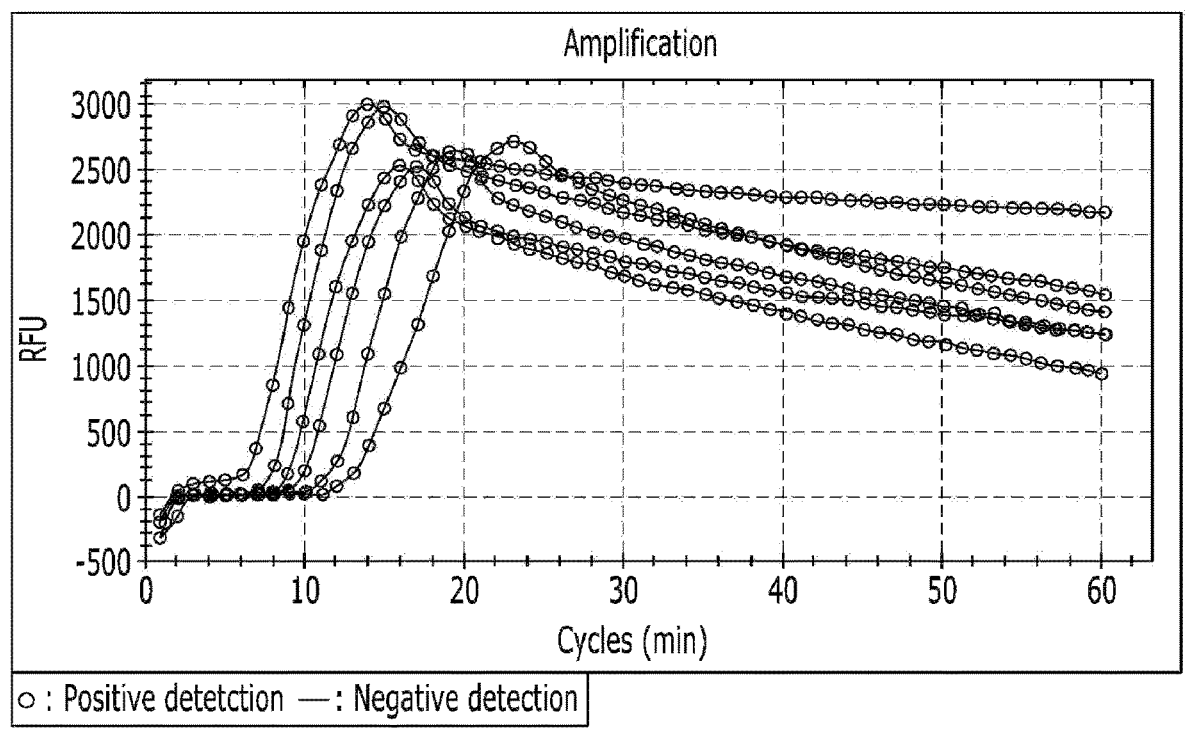

[Fig. 7]
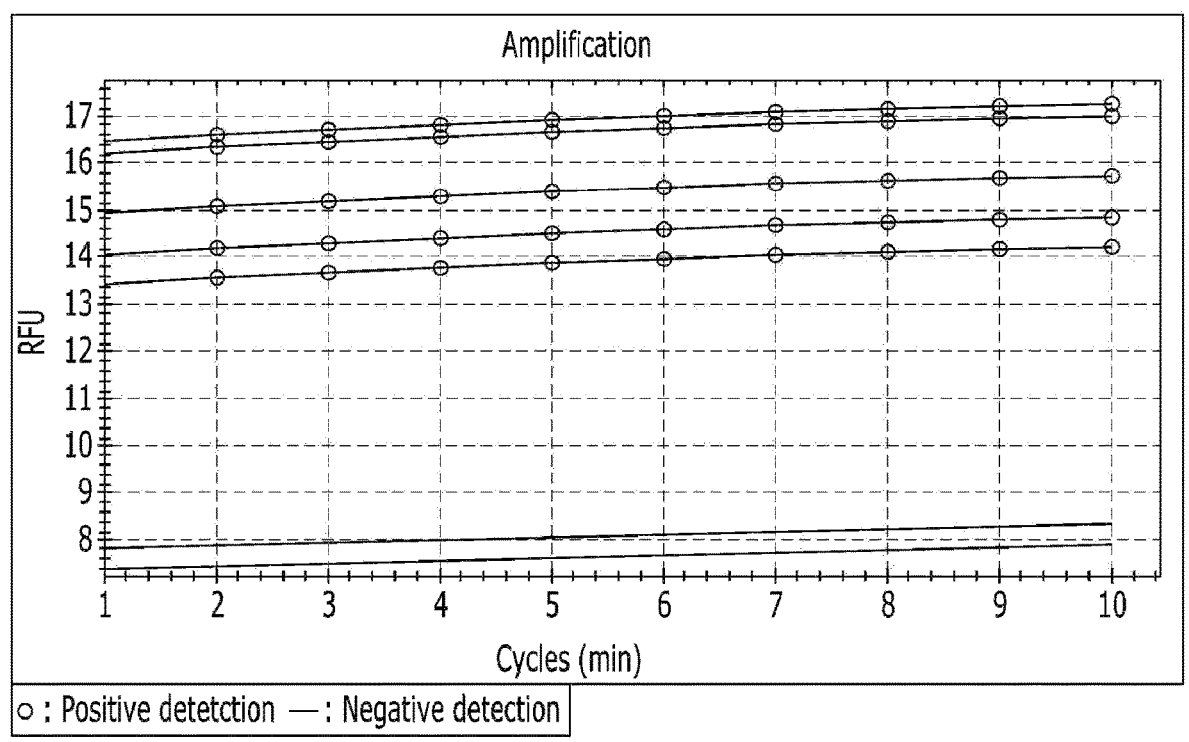

[Fig. 8]
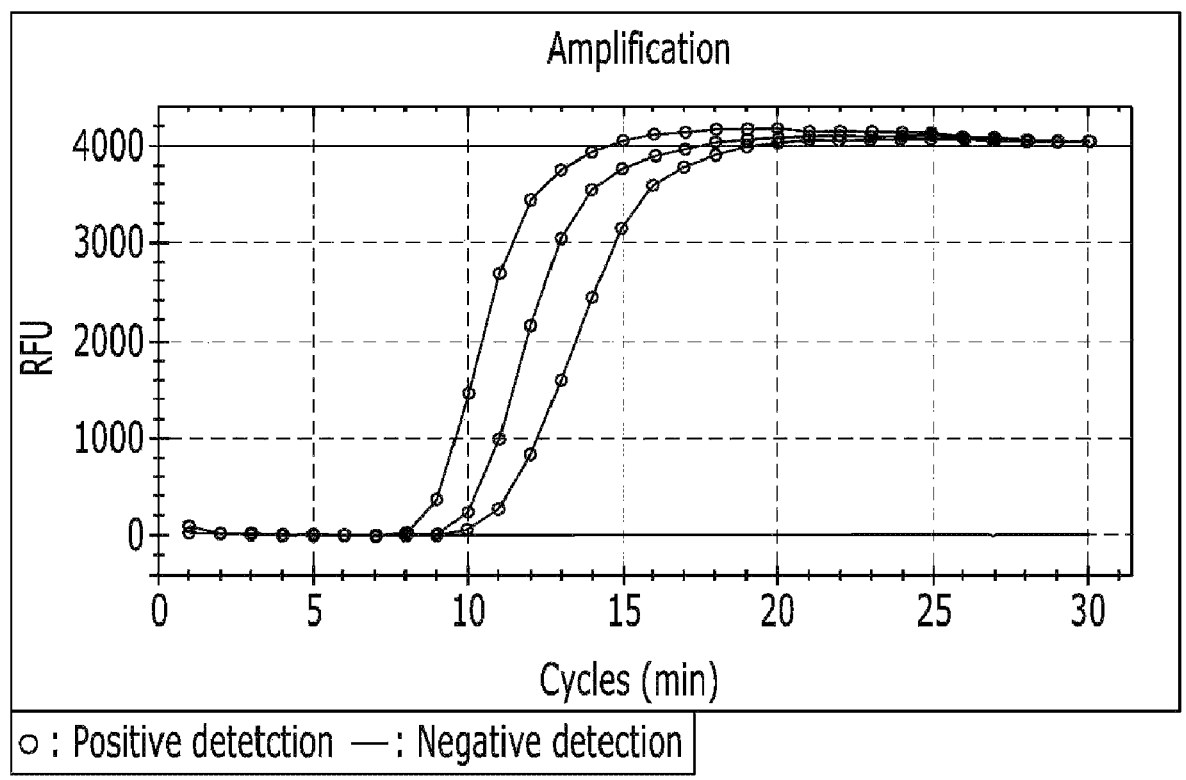

[Fig. 9]
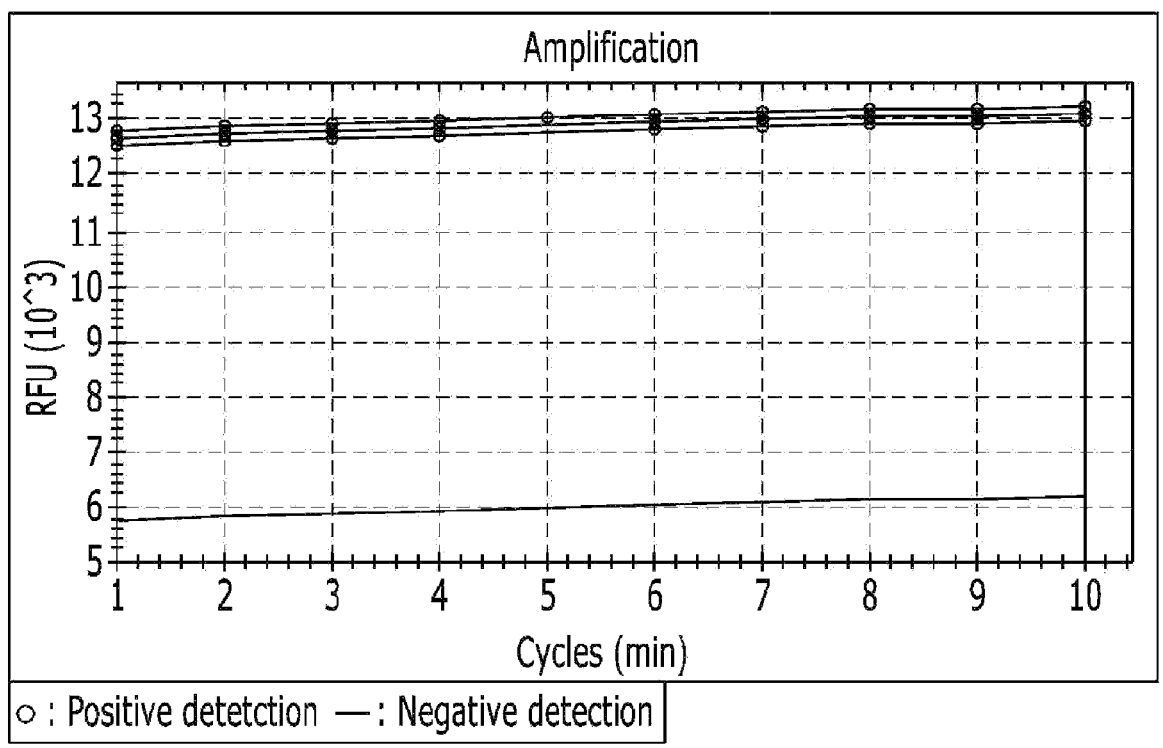

[Fig. 10]
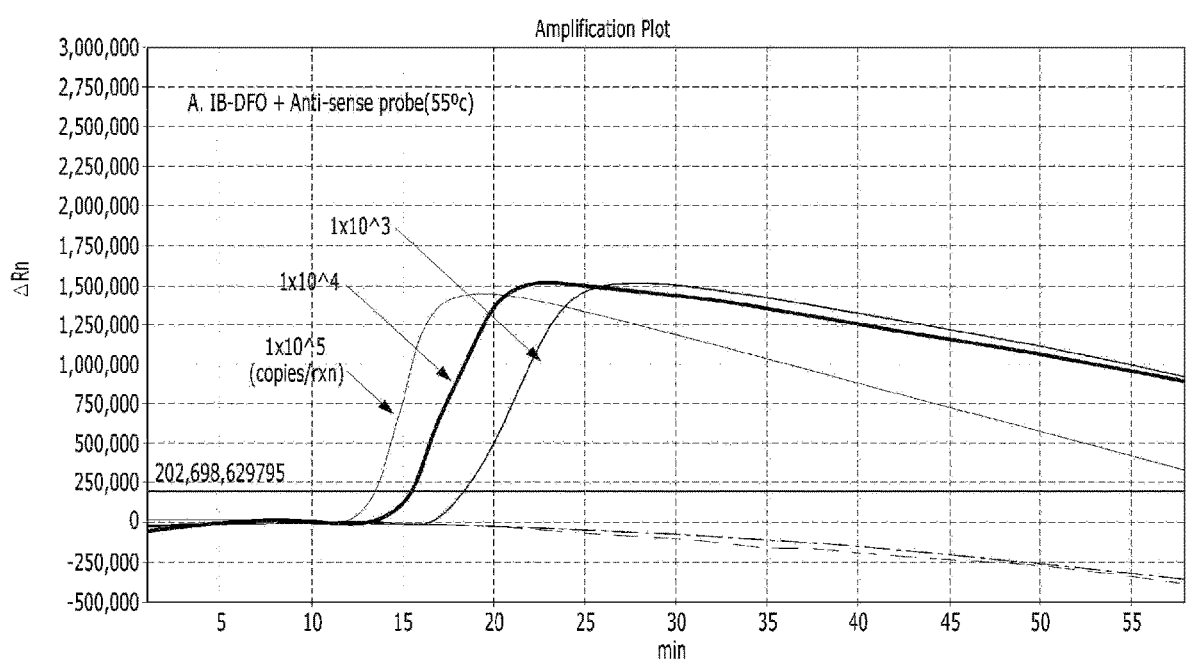

[Fig. 11]
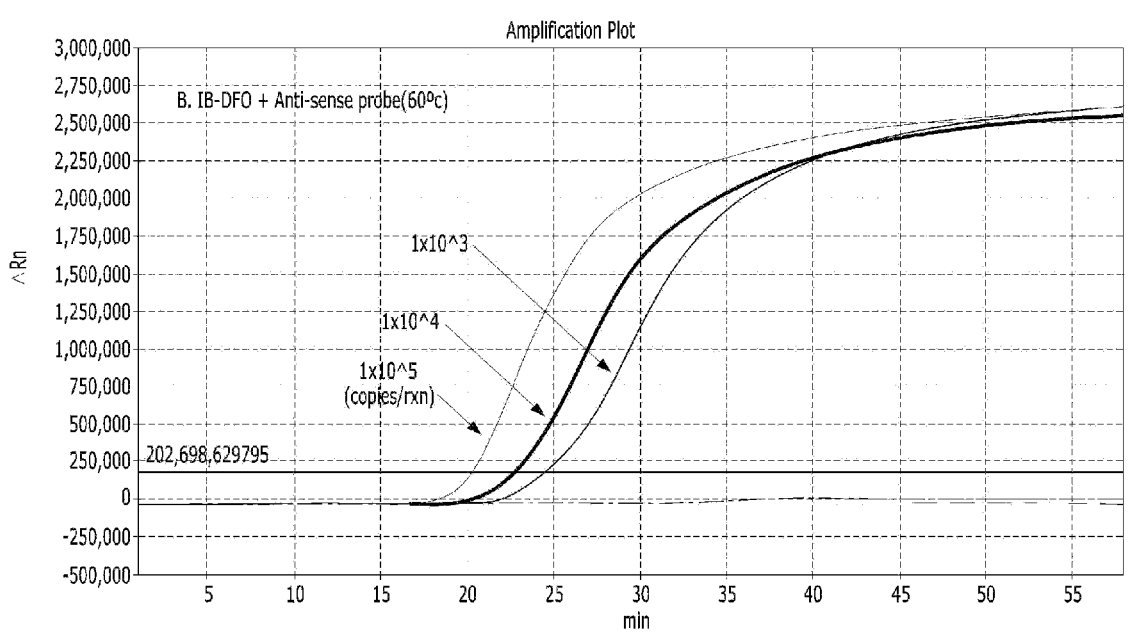

[Fig. 12]
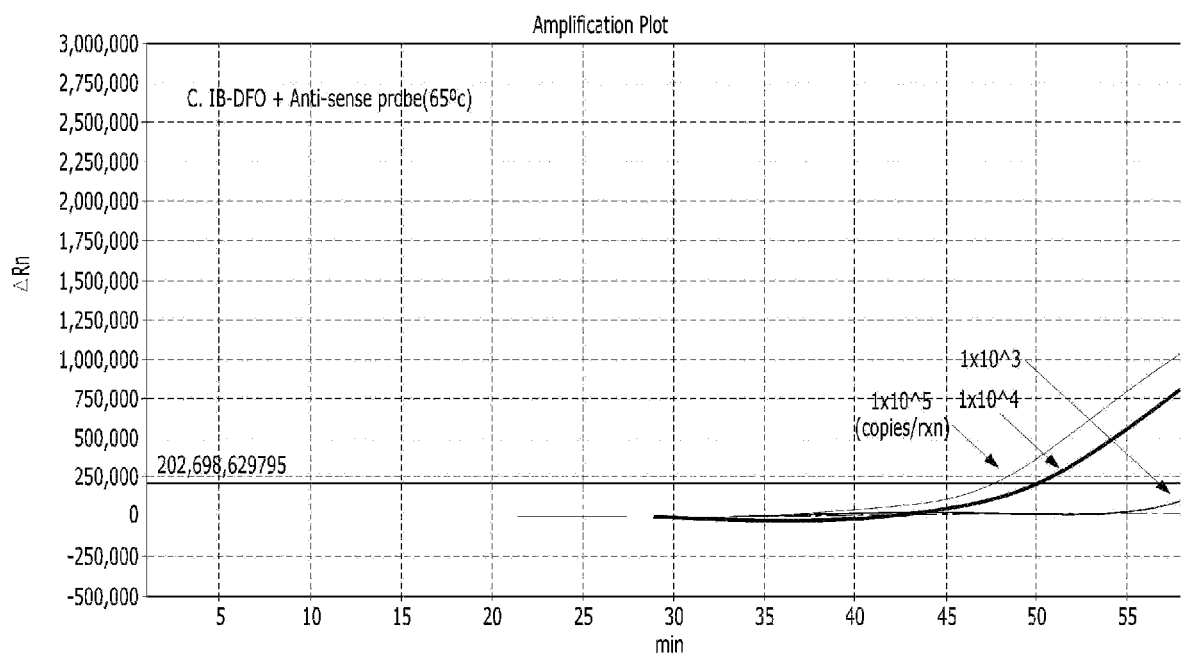

[Fig. 13]
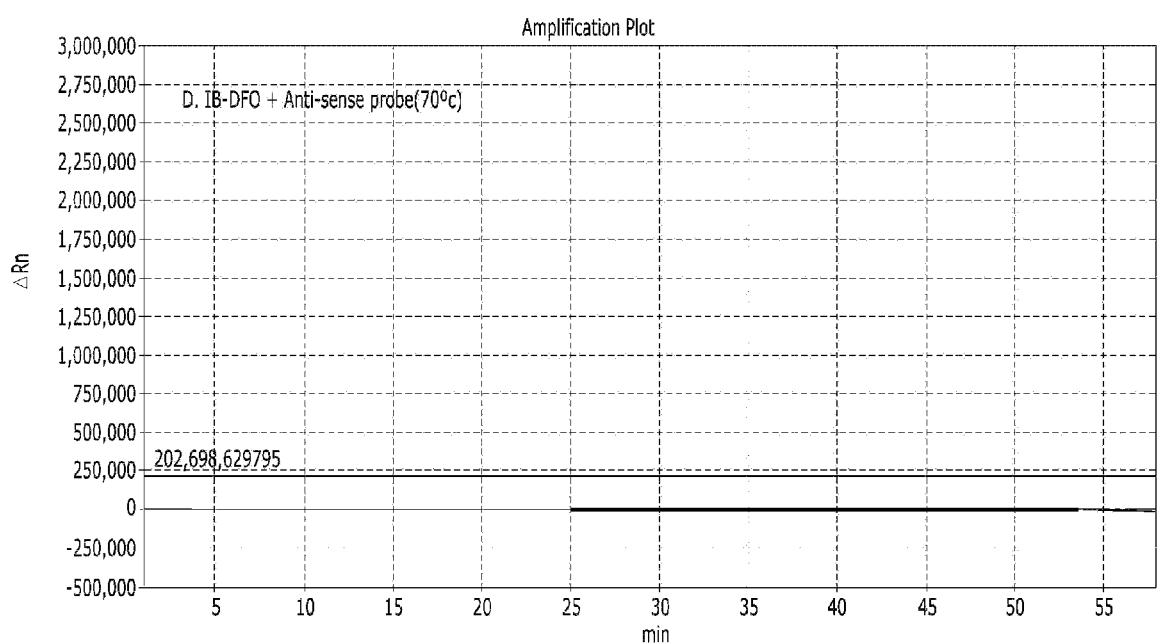

[Fig. 14]
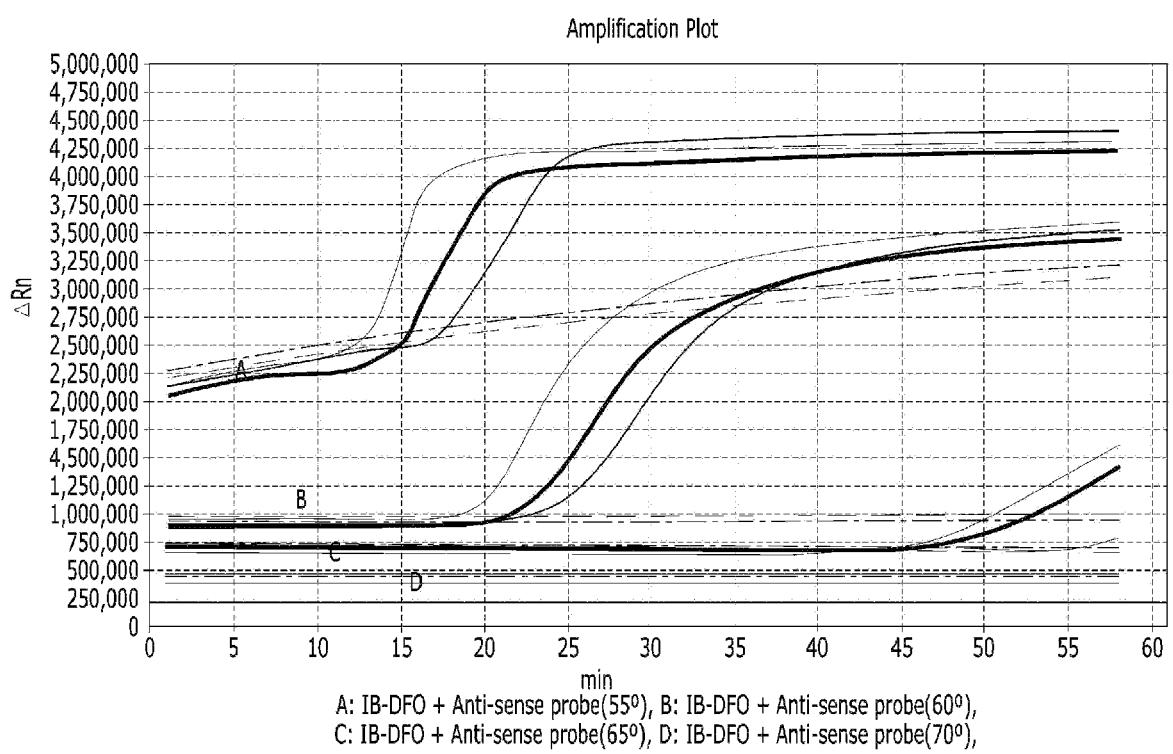

[Fig. 15]
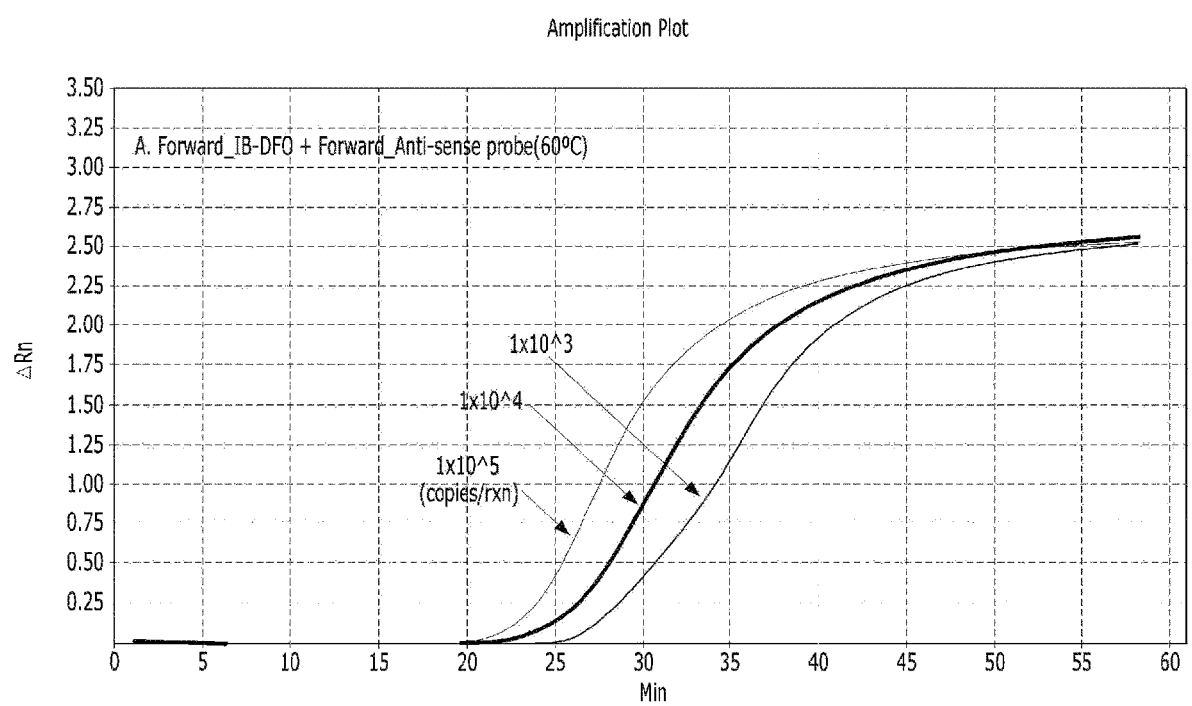

[Fig. 16]
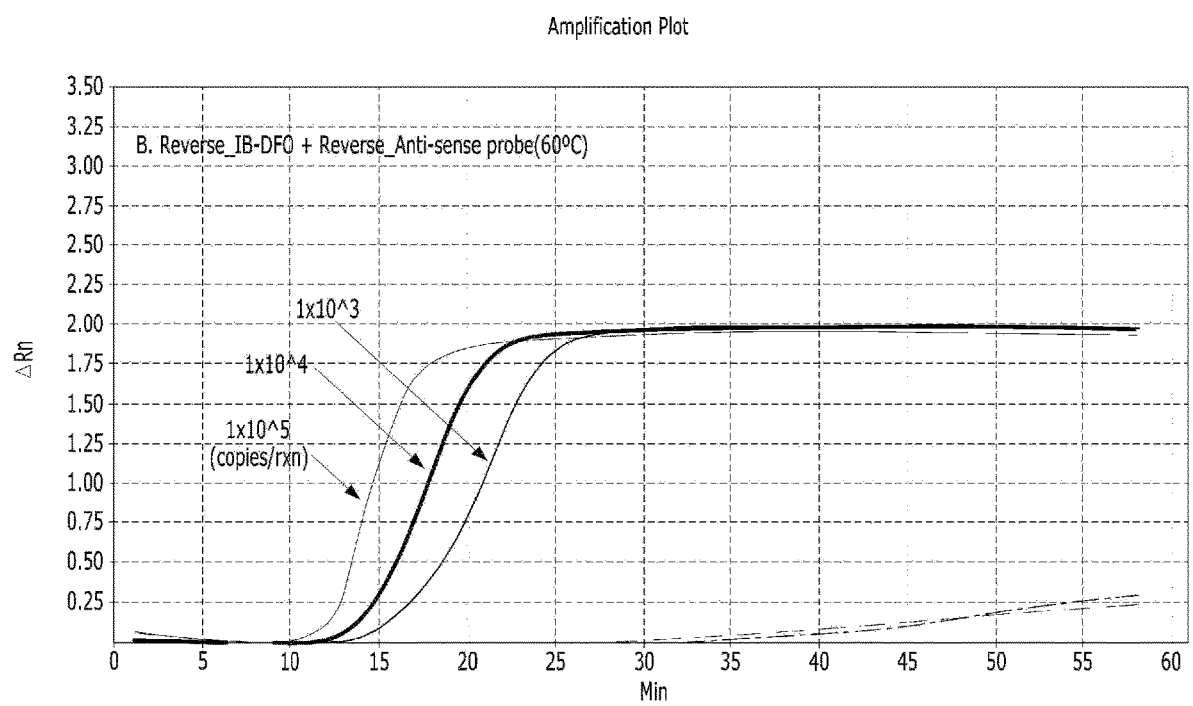

[Fig. 17]
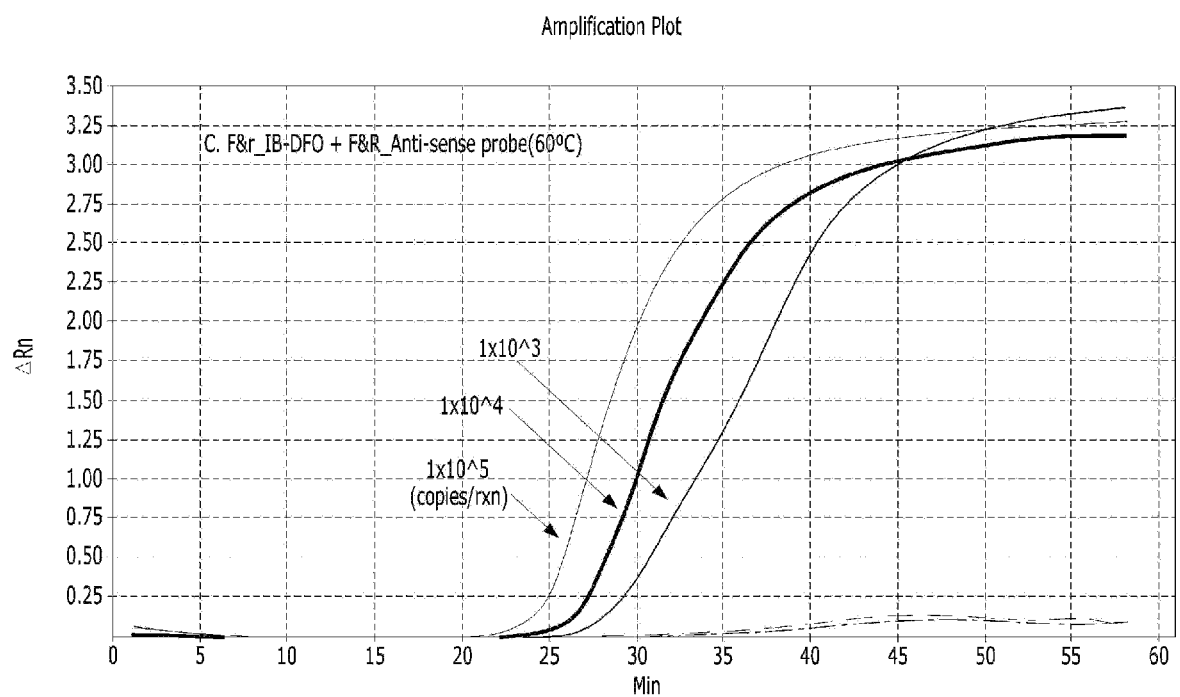

US 11,795,514 B2

ISOTHERMAL BASED-DUAL FUNCTIONAL OLIGONUCLEOTIDE INCLUDING REPORTER DYE, AND QUENCHER FOR ISOTHERMAL NUCLEIC ACID AMPLIFICATION AND MEASUREMENT METHODS USING

TECHNICAL FIELD

The invention relates to an isothermal-based dual functional oligonucleotide containing quencher and reporter dye for an isothermal nucleic acid amplification and a method for nucleic acid amplification and measurement using the same, more specifically an use of isothermal-based dual functional oligonucleotide measuring the presence or absence of the nucleic acid amplification at each of the reaction times through a real-time fluorescence monitoring and detecting the present or absence of the nucleic acid amplification reaction of the reaction product through the measurement of amount of fluorescence at the end-point step, and nucleic acid amplification method and measurement methods by using the same.

BACKGROUND ART

A nucleic acid amplification technique is a technique which is mainly used in a molecular biology and biotechnology fields, which can detect and analyze a small amount of nucleic acid. PCR (Polymerase chain reaction) technology analyzing DNA/RNA using a thermostable enzyme is the most widely used method for the nucleic acid amplification, wherein a double strand DNA is denatured into a single strand DNA; then a temperature is lowered to link a primer to the single strand; the Taq polymerase (thermostable enzyme) is extended to the double strand DNA; and the said procedures are repeated.

A real-time PCR method is a method that a nucleic acid is detected according to a luminescence intensity of fluorescence during PCR procedure, wherein a reporter dye is attached at oligonucleotide 5' end having a complementary sequence corresponding to the PCR reactant intermediate position; a single strand of probe is linked to the complementary sequence during the PCR reaction by the 5'→3' exonuclease activity of the Taq polymerase by adding a single strand of probe wherein a quencher is attached a 3' end; the probe is hydrolyzed from 5' end by the extension reaction of Taq polymerase to make the reporter dye to away from the quencher and thus to emit the florescence and thus mark the amount of fluorescence by the fluorescence detector of the real time PCR equipment. This is a technology which is widely used in the diagnostic field such as a pathogen detection, mutation detection, etc. since a simultaneous multiple-detection detecting two or more of targets can be made by varying the fluorescence detector of the real-time PCR equipment, and has disadvantages that the expensive real-time PCR equipment and skilled technicians are needed.

Isothermal amplification methods detecting DNA/RNA under an isothermal condition without an expensive real-time PCR equipment and detecting nucleic acid within a faster time than PCR method are being developed. For a RNA amplification, there is Transcription Mediated Amplification (TMA), and Nucleic Acid Sequence-Based Amplification (NASBA) methods using an enzyme such as RNA polymerase, reverse transcriptase, and Rnase H, and the Strand Displacement Amplification (SDA) is the method in which the exonuclease-deficient DNA polymerase displaces one existing strand so as to synthesize the double strand of nucleic acid, and Nicking and Extension Amplification Reaction (NEAR) similar to this is the method using a nicking enzyme instead of a restriction enzyme. Helicase-Dependent Amplification (HDA) is the method using the function of Helicase sets the double strand free from 5' end and 3' end, and Recombinase Polymerase Amplification (RPA) similar to this is the method using the recombinase sets free the double strand.

A loop-mediated isothermal amplification (LAMP) is a nucleic acid amplifying technique (Patent No. PCT/JP2000/001919) using the DNA polymerase in which has 4~6 the specific primers and strand displacement.

A band of the smeared pattern is confirmed by the measuring method of LAMP through the electrophoresis analysis of agarose gel and the presence or absence of the nucleic acid amplification reaction of specific gene can be analyzed, but since the reaction tube is opened at the time of the electrophoresis analysis of agarose gel, said method can be a source of the nucleic acid contamination.

Therefore, technologies are developing which can measure without opening the reaction tube to block the source of the nucleic acid contamination pollution source, and a turbidimetry method being generally used in LAMP (Mori. Y. et al., Biochemical and Biophysical Research Communications, 2001, 289:150-154) can confirm the presence of the nucleic acid amplification without opening the reaction tube since the real-time detection and end-point detection are possible by measuring the turbidity having 400 nM of wavelength by the accumulation of white precipitation due to magnesium pyrophosphate ($Mg_2P_2O_7$) according to the increase of the amplification reaction of the isothermal nucleic acid. However, it has the disadvantage that the multiple-detections at the same time such as a discrimination of two or more of targets is impossible, and the accuracy for the measuring method is low due to the precipitation of the magnesium pyrophosphate.

In LAMP, the fluorescence detection method for the real-time measuring the presence of the nucleic acid amplification removed the occurrence of contamination by measuring only the fluorescence material without opening the reaction tube, and has advantage which can remove the reduction of the accuracy due to the generation of precipitating materials.

In LAMP, the double-strand chain-specific intercalater such as SYBR Green I is added to the reaction solution and the amount of fluorescence is increased according to the increase of nucleic acid amplification reaction product and thus the real-time measurement is possible. Since the SYBR Green I which is also used in the real-time PCR amplification reaction does not confirm the nucleic acid amplification product in a sequence-specific manner, the degree of fluorescence is measured even in the occurrence of primer dimer and thus the temperature is slowly raised up to 95° C. after the real-time measurement to discriminate the non-specific reaction and the annealing temperature of the nucleic acid amplification reaction product is measured for judging the non-specific reaction so that one can confirm the presence of the detection, and the same time (simultaneous) multiple-detection such as two or more target distinctions is impossible.

It has developed technologies for detecting fluorescence to the nucleic acid PCR sequence specific manner by LAMP. The assimilation probe is a method for real-time measurement (Patent No. PCR/US11/41540) using the FRET (Fluorescence Resonance Energy Transfer) principles with two strands of probe designed in a sequence-specific manner of nucleic acid amplification. One of two strands is attached to 5' end of reporter dye, and other strand is located at 3' end of the quencher. The number of oligonucleotides used in LAMP nucleic acid amplification includes 6 types of a number of primer, and the assimilation probe designs one strand of probe that the reporter dye is attached to 5' end for one of the loop primers, and designs a part of the sequence complementary to this to design other strand of probe that the quencher is attached at 3' end and thus it should synthesize 7 types of oligonucleotides; and the assimilation probe slowly decreases the temperature of two probes from the high temperature to low temperature prior to LAMP reaction to synthesize as a pair of probes and then used in the amplification of nucleic acid. In LAMP, for the real-time of detection of the gene sequence-specific real-time detection, the inhibiting effect of LAMP reaction in the nucleic acid amplification reaction is occurred by using the assimilation probe, and thus the detection time and real time measurement time get longer.

As the fluorescence detecting method using the probe similar to the assimilation probe, there is a method using a pair of probes which is designed so that the fluorophore-labeled primer/probe and quencher-labeled probe have the complementary sequence (Patent No. PCT/JP2012/077596). By designing the annealing temperature of the fluorescence-labeled probe differently from that of the quencher-labeled probe, only the fluorescence-labeled probe is annealed on the target gene-specific sequence to react during LAMP nucleic acid amplification reaction, and after the completion of LAMP nucleic acid amplification reaction, the remaining fluorescence probe is linked with the quencher probe by lowering the temperature and then detect the amount of fluorescence. The said pair of probes cannot be confirmed in real-time detection, and one oligonucleotide should also be added and designed like the assimilation probe.

Although the technologies for solving the false-positive reaction by the contamination and sensitively measuring the amplification of target nucleic acid present in a low concentration and by confirming the nucleic acid amplification without opening the reaction tube through the real-time detection and amount of fluorescence measurement in LAMP nucleic acid amplification reaction, the methods have limitations which are not specific to the target nucleic acid sequence such as turbidimetry and intercalator fluorescence measurement cannot confirm the presence or absence of the non-specific amplification, and the simultaneous multiple-nucleic acid detection is impossible, and the methods using the probes can be designed in a target gene-sequence specific manner and use various reporter dyes and quenchers, and thus the simultaneous multiple-nucleic acid detection can be carried out. However, it requires the design of oligonucleotide called as the quencher probe to form a pair of probes in addition to 6 types of oligonucleotides used in LAMP, and a process is added that a pair of probes is synthesized prior to the preparation of reactant and should be added to the reactant. Also, the design position of the pair of probes should be designed as the fluorescence probe by replacing the loop primer. Since the loop primer is proceed with the next procedure by the annealing after that the loop in the structure of dumbbell upon LAMP reaction is formed, the time that the fluorescence is measured is measured with the delayed time of the fluorescence detection than the time that the actual nucleic acid is amplified. There are disadvantages that the assimilation probe provides the reactivity of LAMP with an inhibitory effect, and in the case of the method using the fluorescence probe and quencher probe the real-time detection cannot be made, and the detection can be made under the condition that the temperature should be lowered after the completion of the reaction temperature.

DISCLOSURE

Technical Problem

The present invention is derived so as to solve said problems and meet said needs, and the purpose of the present invention is to develop the technology that for the nucleic acid amplification reaction of LAMP, in addition to 4~6 types of oligonucleotide the oligonucleotides additionally designed are not needed; the sequence-specific detection of the target gene is possible; and the real-time detection which is not the detection after the completion of the reaction is possible, and to measure the amplification product occurred during LAMP isothermal amplification process on a real-time basis, and to provide a method that a simultaneous multiple detection is possible.

Technical Solution

In order to achieve said purpose, the present invention provides an oligonucleotide, wherein parts of sequences among sequences except for 3' end on Forward Inner Primer or Reverse Inner Primer for a loop-mediated isothermal nucleic acid amplification reaction (LAMP) for a specific sequence of a target gene are replaced with internal dT, internal dG, internal dC, internal dA, internal dU, internal dR; the reporter dye or quencher is placed in this site; and all or a part of the sequences form the double-strand at a certain temperature or lower, having one or more of bubble structures.

In one embodiment of the present invention, the oligonucleotide is preferably located within a range of 21 to 33-mer with respect to the reporter dye and the quencher interval, but is not limited thereto In another embodiment of the present invention, it is preferable that the oligonucleotide is used separately or together with a forward internal probe and a reverse internal probe, but is not limited thereto.

In one example of the present invention, the reporter dye of the oligonucleotide is one of FAM, TET, HEX, TAMRA, ROX, TEXAS RED, CY3, and CY5, or is preferably an emission wavelength band of 450 to 685 nm; and the quencher of the oligonucleotide is TAMRA, DABCYL, Black Hole Quencher 1, or 2, or is preferably in the range of 500 to 705 nm absorption wavelength band, but is not limited thereto.

In one embodiment of the present invention, the oligonucleotide preferably has one to four bubble structures; and the oligonucleotide preferably has a melting temperature of 30 to 70° C. for unwinding from a double strand to a single strand, but is not limited thereto.

In one example of the present invention, the oligonucleotide is preferably one of the oligonucleotides described in SEQ ID NOS: 5 to 8 and SEQ ID NOS: 15 to 16, but is not limited thereto.

The present invention also provides a method for performing loop-mediated isothermal nucleic acid amplification (LAMP) or reverse transcription (RT)-LAMP reactions for fluorescence detection of real time nucleic acid amplification at isothermal temperature using the oligonucleotide of the present invention.

Also, the present invention provides a method for performing loop-mediated isothermal nucleic acid amplification (LAMP) or reverse transcription (RT)-LAMP reactions for fluorescence detection of end-point nucleic acid amplification under the condition of isothermal temperature or two or more of temperatures using the oligonucleotide of the present invention.

In the method of the present invention, it is preferable that the oligonucleotide is used separately or together with a forward internal probe and a reverse internal probe; and the isothermal temperature condition of the above method is preferably in the range of 50 to 75° C., but is not limited thereto.

In the method of the present invention, it is preferable that the method is performed on DNA and cDNA nucleic acids, and the method is preferable to perform a one step reaction on a specific gene after a reverse transcription reaction on an RNA nucleic acid, but is not limited thereto.

The present invention also provides a kit for separately or simultaneously multiplex-amplifying a specific gene for an infectious disease, hereditary disease, drug resistance, drug resistance or susceptibility specimen comprising the oligonucleotide of the present invention.

The present invention also provides a composition for amplifying an Ebola virus nucleic acid comprising the oligonucleotide of the present invention as an active ingredient.

Also, the present invention provides a composition for an isothermal nucleic acid amplification reaction comprising the oligonucleotide of the present invention as an active ingredient.

In one embodiment of the present invention, the composition preferably includes oligonucleotides of SEQ ID NOS: 1 to 18, but is not limited thereto.

The present invention also provides a method for performing isothermal nucleic acid amplification reaction on DNA, RNA, or cDNA by using the oligonucleotide of the present invention in combination with an anti-sense probe.

In one embodiment of the present invention, the anti-sense probe is preferably designed and used within 55 to 65° C., but is not limited thereto.

In another embodiment of the present invention, the oligonucleotide and the anti-sense probe are preferably used separately or together in the forward and reverse positions, but are not limited thereto.

In another embodiment of the present invention, the anti-sense probe preferably has one of the sequences set forth in SEQ ID NOS: 19 to 23, but is not limited thereto.

Hereinafter, the invention is illustrated.

Abbreviations used in the present invention are as follows:

Internal dT: Internal Amino-C6 (or C2)-deoxythymine, Internal dA: Internal Amino-C6-deoxyadenocine, Internal dC: Internal Amino-C6-deoxycytidine, Internal dG: Internal Amino-C6-deoxyguanosine, Internal dU: Internal Amino-C6-deoxyuridine, Internal dR: Internal Amino-C6-deoxyribose The present invention provides with an use of isothermal-based bifunctional oligonucleotides, a nucleic acid amplification and determination methods using such oligonucleotides, wherein Forward inner Primer (FIP) and Reverse Inner Primer (RIP) of Loop-mediated isothermal amplification (LAMP) method are designed as one oligonucleotide, one or more bubble structures are formed between two gene sites, and except for the 3' end, a 5' end or a thymine site is modified with internal dT and a reporter dye or a quencher is attached on the site, and one reporter dye and one quencher are positioned on one IB-DFO to perform the two functions of primer and probe, real-time fluorescence monitoring is performed in isothermal nucleic acid amplification reaction to determine whether the nucleic acid amplification is made in every time and the fluorescence for the reaction product is determined through monitoring the fluorescence in end-point step to detect whether the isothermal nucleic acid amplification reaction is made.

The present invention provides with an oligonucleotide wherein modifying Thymine base with internal dT, or modifying Adenine, Thymine, Guanine, Cytosine or Uridine base with internal dR on the sequence except 3' end of FIP or RIP among primers for LAMP isothermal nucleic acid amplification reaction with regard to a certain sequence of the target gene, and by placing the reporter dye or quencher on such sites and all or a part of the sequence forms double strands at below a certain temperature and has one or more of bubble structure.

The oligonucleotide of the present invention provides an isothermal nucleic acid amplification reaction mixture containing at least one isothermal-based bifunctional oligonucleotide for isothermal nucleic acid amplification of a specific gene sequence of target DNA, cDNA, and RNA.

The present invention also relates to a mixture for LAMP nucleic acid amplification reaction comprising Tris-HCl, KCl, (NH4) 2SO4, MgCl2, MgSO4, Betaine, Dithiothreitol (DTT), Triton X-100, Teen-20, dNTPs, Bovine serum albumin Dimethyl sulfoxide (DMSO), Formamide, Single strand binding protein, Pyrophosphate, Pyrophosphatase, etc., and also comprising IB-DFO in combination with DNA polymerase having 5'→3' exonuclease (−), 3' exonuclease (−), strand displacement activity. And, it relates to an use of the mixture for RT-LAMP nucleic acid amplification reaction comprising RNase inhibitor and Reverse transcriptase such ad Avian Myeloblastosis Virus (AMV) Reverse transcriptase, Molony Murine Leukemia Virus (MMLV) Reverse transcriptase, etc., and IB-DFO in combination with DNA polymerase having thermostable Reverse transcriptase and Reverse transcriptase functions.

The oligonucleotides of the present invention provide oligonucleotides in which the reporter dye and a quencher are located within 21 to 33 mer interval, but are not limited thereto.

The present invention provides the oligonucleotide which is characterized in that FIP-IB-DFO, a forward probe of the oligonucleotide, and RIP-IB-DFO, a reverse probe, are used separately or together.

The present invention provides with an oligonucleotides comprising one of PAM, TEL HEX, TAMRA, ROX, TEXAS RED, CY3 and CY5 as a reporter dye of the oligonucleotides, and having the emission wavelength band of 450 to 685 nm.

The present invention provides with an oligonucleotide comprising TAMRA, DABCYL, and Black Hole Quencher 1, 2 as the oligonucleotide quencher and comprising an absorption wavelength band of 500 to 705 nm, but is not limited thereto.

The present invention provides LAMP and RT-LAMP reaction methods for detecting real-time nucleic acid amplification fluorescence detection using an oligonucleotide of the present invention at the isothermal temperature.

The present invention provides LAMP and RT-LAMP reaction method for detecting end-point nucleic acid amplification fluorescence at isothermal or two or more temperatures using oligonucleotides of the present invention.

The method provides a mixture comprising an IB-DFO concentration of 0.2-1.6 uM of the oligonucleotide either separately or together with PIP or RIP, but is not limited thereto.

The present invention provides a method wherein the isothermal temperature condition of the LAMP reaction method using the oligonucleotide of the present invention has a range of 50 to 75° C.° C., but is not limited thereto.

The present invention provides a method for performing LAMP reaction method on DNA and cDNA nucleic acid using oligonucleotide of the present invention.

The present invention provides a method for performing a reverse transcription reaction on RNA nucleic acid using the oligonucleotide of the present invention and then performing a one-step reaction on a specific gene.

The oligonucleotides of the present invention provide oligonucleotides having one to four bubble structures.

The present invention provides with an oligonucleotide characterized in that an annealing temperature in which a double strand is unwound into a single strand is 30 to 70° C., but is not limited thereto.

The present invention provides a kit for amplifying a specific gene for DNA, cDNA, and RNA of an infectious disease, hereditary disease, drug resistance, drug resistance or susceptible sample including the oligonucleotide of the present invention, individually or multiple simultaneously.

The oligonucleotides of the present invention provide with oligonucleotide sequences of SEQ ID NOS: 1 to 18 for the subtypes of Ebola virus, Bundibugyo and Reston, and LAMP and RT-LAMP primer sequences.

Advantageous Effects

As can be seen from the present invention, the present invention has advantages that oligonucleotides additionally designed in addition to 4 to 6 types of oligonucleotides for LAMP nucleic acid amplification reaction are not needed, the amount of fluorescence according to the nucleic acid amplification of the target gene specific sequence for DNA and RNA is detected and it can be detected even after finishing the reaction, and simultaneous multiple analysis can be made by determining the amount of fluorescence using different reporter dyes according to the target gene in a tube after finishing the reaction or in real-time, as a method that can detect the amount of fluorescence in real time.

DESCRIPTION OF DRAWINGS

FIG. 1 shows a result determining a real-time fluorescence for LAMP nucleic acid amplification reaction according to the number of mer (distance) of 33, 25, 21 mer between the reporter dye and the quencher of the oligonucleotide (IB-DFO) of the present invention.

FIG. 2 shows result of real-time fluorescence measurement for LAMP nucleic acid amplification reaction using the IB-DFO designed with forward inner primer (FIP) and reverse inner primer (RIP) of the oligonucleotide (IB-DFO) of the present invention, separately.

FIG. 3 shows the result of real-time fluorescence measurement for LAMP nucleic acid amplification reaction by applying IB-DFO designed with forward inner primer (HP) and reverse inner primer (RIP) of the oligonucleotide (IB-DFO) of the present invention separately or together.

FIG. 4 shows a result determining the real-time fluorescence for LAMP nucleic acid amplification reaction using oligonucleotide (IB-DFO) of the present invention as FIP and IB-DFO designed by FIP sequence in FIP:FIP-IB-DFO ratio of 0:1.6 uM/0.4:1.2 uM/0.8:0.8 uM/1.2:0.4 uM/1.4:0.2 uM/1.6:0 uM.

FIG. 5 shows a result determining an end-point fluorescence for LAMP nucleic acid amplification reaction using oligonucleotide (IB-DFO) of the present invention as FIP and IB-DFO designed by PIP sequence in FIP:FIP-IB-DFO ratio of 0:1.6 uM/0.4:1.2 uM/0.8:0.8 uM/1.2:0.4 uM/1.4:0.2 uM/1.6:0 uM.

FIG. 6 shows the result determining the real-time fluorescence for LAMP nucleic acid amplification with plasmid DNA as a template using the oligonucleotide (IB-DFO) of the present invention.

FIG. 7 shows a result determining the end-point fluorescence for LAMP nucleic acid amplification reaction with plasmid DNA as a template using the oligonucleotide (IB-DFO) of the present invention.

FIG. 8 shows a result determining the real-time fluorescence for a one-step RT-LAMP nucleic acid amplification reaction with an RNA transcript as a template using the oligonucleotide (IB-DFO) of the present invention.

FIG. 9 shows a result determining end-point fluorescence measurement for the one-step RT-LAW nucleic acid amplification reaction with an RNA transcript as a template using oligonucleotide (IB-DFO) of the present invention.

FIGS. 10 to 13 show results determining the real-time fluorescence for LAMP nucleic acid amplification reaction with plasmid DNA as a template using the oligonucleotide (IB-DFO) of the present invention and an anti-sense probe comprising a quencher designed by temperature (55, 60, 65, 70° C.).

FIG. 14 shows a result of Rn vs min (non-normalization) type, which determines the real-time fluorescence for the LAMP nucleic acid amplification reaction with plasmid DNA as a template using an oligonucleotide (IB-DFO) of the present invention and an anti-sense probe comprising quencher designed at different temperatures (55, 60, 65, 70° C.).

FIGS. 15-17 show results determining the real-time fluorescence for LAMP nucleic acid amplification reaction using the oligonucleotide (IB-DFO) as forward (F) or reverse (F) or forward (F) and reverse (R), with plasmid DNA as a template together with anti-sense probe comprising quencher designed by the sequence complementary to the oligonucleotide at 60° C.

MODE FOR INVENTION

Hereinafter, the present invention will be described in detail with reference to Examples. Provided that, the following examples are for illustrative purposes only and are not intended to limit the scope of the present invention.

Example 1: Analysis of Fluorescence Detection Effect According to Distance (Mer Number) Between Reporter Dye and Quencher of the Oligonucleotide (IB-DFO) of the Present Invention To observe the fluorescence detection effect of LAMP isothermal nucleic acid amplification reaction according to the distance (mer number) between the reporter dye and the quencher of the IB-DFO of the present invention, 4 types of primers for LAMP isothermal nucleic acid amplification for the L segment (Polymerase) site sequence of Bundibugyo, one of the subtypes of Ebola virus, were designed by PrimerExplorer V4 Software (http://primerexplorer.jp/elamp4.0.0/index.html).

The designed primers are EB_B_F3 (SEQ ID NO: 1), EB_B_R3 (SEQ ID NO: 2), EB_B_FIP (SEQ ID NO: 3) and EB_B_RIP (SEQ ID NO: 4), and IB-DFO was made by replacing Thymine with internal dT on EB_B_FIP primer sequence and modifying FAM with a reporter dye at this site, and by replacing Thymine at the interval positions of 33 (EB_B_FIP_P2, SEQ ID NO: 5), 25 (EB_B_FIP_P2.5, SEQ ID NO: 6), 21 mer (EB_B_FIP_P3, SEQ ID NO: 7) with internal dT and attaching BHQ1 quencher at this sites. The Melting temperature at which three IB-DFOs were unwound from a double strand to a single strand was 54° C.

The isothermal nucleic acid amplification reaction for the IB-DFO oligonucleotides was performed by using 20 mM Tris-HCl (pH 8.8), 50 mM KCl, 10 mM MgSO4, 10 mM (NH4) 2SO4, 0.1% Tween-20, 1.4 mM dNTP each, 0.5 M Betaine, 8 U Bst DNA polymerase (MCLAB, CA, USA), and 0.2 uM of EB_B_F3 and EB_B_R3; adding 1.2 uM of EB_B_FIP and 1.6 uM of EB_B_RIP to the mixture; and additionally adding 0.4 uM of IB-DFO. Bundibugyo L segment (gb:FJ217161, 521 bp) of Ebola virus was constructed by gene synthesis and used as a concentration of $1 \times 10^7$, $1 \times 10^5$, $1 \times 10^3$, 0 copies/reaction. The real-time fluorescence detection for isothermal nucleic acid amplification was performed at 65° C. for 60 minutes, and the amount of fluorescence was measured using CFX-96 (Bio-Rad, CA, USA) real-time fluorescence measurement equipment in every 1 minute.

FIG. 1 shows the results of amplification of LAMP isothermal nucleic acid for reporter dye and quencher interval of IB-DFO using IB-DFO designed at 33, 25, and 21-mer intervals, wherein the detected similar fluorescence time was 11.98 min, 12.03 min, 12.16 min, respectively, for $1 \times 10^7$ copies/reaction: 15.3 min, 15.28 min and 15.73 min, respectively, for $1 \times 10^5$ copies/reaction: and 20.42 min, 20.09 min and 22.29 min, respectively, for $1 \times 10^3$ copies/reaction; and the fluorescence signal was not detected for 0 copies/reaction with addition of D.W. only. Therefore, for the reporter dye and quencher of IB-DFO, the amount of fluorescence were measured within 21 to 33 mers, and among these, the highest RFU (Relative fluorescence unit) was confirmed in 25-mer IB-DFO.

Example 2: Analysis for the Effect Using the Oligonucleotide (IB-DFO) of the Present Invention at Forward and Reverse Positions In order to observe the fluorescence detection effect according to LAMP isothermal nucleic acid amplification reaction when the IB-DFO of the present invention was used in the forward or reverse position, four types of primers for LAMP isothermal nucleic acid amplification were designed by PrimerExplorer V4 Software on the L segment (Polymerase) site sequence of Bundibugyo, one of the subtypes of Ebola virus. The designed primers were EB_B_F3 (SEQ ID NO: 1), EB_B_R3 (SEQ ID NO: 2), EB_B_FIP (SEQ ID NO: 3) and EB_B_RIP (SEQ ID NO: 4); and IB-DFO used EB-B_FIP_P2 (SEQ ID NO: 5) obtained by replacing Thymine with internal dT on EB_B_FIP primer sequence, replacing FAM with the reporter dye on this site, replacing Thymine in 33 mer interval position with internal dT and attaching BHQ 1 on this site, and BHQ1-EB_B_RIP_P2 (SEQ ID NO: 8) designated by placing FAM reporter dye and BHQ1 quencher in 30 mer interval on EB_B_RIP primer sequences.

The isothermal nucleic acid amplification reaction for the IB-DFO oligonucleotides was performed by using 20 mM Tris-HCl (pH 8.8), 50 mM KCl, 10 mM MgSO4, 10 mM (NH4) 2SO4, 0.1% Tween-20, 1.4 mM dNTP each, 0.5 M Betaine, 8 U Bst DNA polymerase (MCLAB, CA, USA) and 0.2 uM of each EB_B_F3 and EB_B_R3, and adding 1.2 or 1.6 uM of EB_B_FIP and 1.2 or 1.6 uM of EB_B_RIP to the mixture, and additionally adding 0.4 uM of EB_B_FIP_P2 and EB_B_RIP_P2, separately. Bundibugyo L segment (gb: FJ217161, 521 bp) of Ebola virus was constructed through a gene synthesis and then used in the concentration of $1 \times 10^7$, $1 \times 10^5$, $1 \times 10^3$, 0 copies/reaction concentration. The real-time fluorescence detection for isothermal nucleic acid amplification was performed at 65° C. for 60 minutes, and the amount of fluorescence was measured using CFX-96 (Bio-Rad, CA, USA) real-time fluorescence measurement equipment in every 1 minute.

FIG. 2 shows the results of LAMP isothermal nucleic acid amplification reaction using IB-DFO designed with FIP and RIP individually. Wherein similar fluorescence detection time was 12.3 min and 13.02 min for $1 \times 10^7$ copies/reaction, respectively, in reactions containing EB_B_FIP_P2 or EB_B_RIP_P2; 15.92 min and 16.13 min, respectively for $1 \times 10^5$ copies/reaction; 15.92 min and 16.13 min, respectively for $1 \times 10^5$ copies/reaction; and 18.94 min and 18.59 min, respectively, for $1 \times 10^3$ copies/reaction: and no fluorescence signal was detected for 0 copies/reaction with the addition of D.W only. Therefore, the real-time fluorescence detection for a similar LAMP isothermal nucleic acid amplification was confirmed irrespective of FIP and RIP positions in IB-DFO design.

Example 3: Analysis of Fluorescence Detection Effect when the Oligonucleotides of the Present Invention (IB-DFO) were Used Individually or Together at Forward and Reverse Positions In order to observe the fluorescence detection effect according to LAMP isothermal nucleic acid amplification reaction, when the IB-DFO of the present invention was used in the forward or reverse position, six types of primers for LAMP isothermal nucleic acid amplification were designed by PrimerExplorer V4 Software on the L segment (Polymerase) site sequence of Reston, one of the subtypes of Ebola virus. The designed primers were EB_R_F3 (SEQ ID NO: 9), EB_R_R3 (SEQ ID NO: 10), EB_R_FIP (SEQ ID NO: 11), EB_R_RIP (SEQ ID NO: 12), Res_LP (SEQ ID NO: 13) and Res_RLP (SEQ ID NO: 14); and IB-DFO used EB-R_FIP_P2 (SEQ ID NO: 15) obtained by replacing Thymine with internal dT on EB_R_FIP primer sequence, replacing FAM with the reporter dye on this site, replacing Thymine in 31 mer interval position with internal dT and attaching BHQ 1 on this site, and EB_R_RIP_P2 (SEQ ID NO: 16) designated by placing FAM reporter dye and quencher in 33 mer interval on EB_R_RIP primer sequences.

The isothermal nucleic acid amplification reaction for the IB-DFO oligonucleotides was performed by using 20 mM Tris-HCl (pH 8.8), 50 mM KCl, 10 mM MgSO4, 10 mM (NH4) 2SO4, 0.1% Tween-20, 1.4 mM dNTP each, 0.5 M Betaine, 8 U Bst DNA polymerase (MCLAB, CA, USA) and 0.2 uM of each EB_R_F3 and EB_R_R3, and 0.8 Um of Res_LP and Res_RLP, adding 1.2 or 1.6 uM of EB_R_FIP and 1.2 or 1.6 Um of EB_R_RIP to the mixture, and adding 0.4 uM of EB_R_FIP_P2 and EB_R_RIP_P2, separately. EB_R_FIP_P2 and EB_R_RIP_P2 were added in amounts of 0.2 uM, respectively, under the condition that they used together, and EB_R_FIP and EB_R_RIP primer were in amounts of 1.4 uM, respectively. Reston L segment (gb: JX477166, 410 bp) of Ebola virus was constructed through a gene synthesis and then used in the concentration of $1 \times 10^4$, $1 \times 10^3$ copies/reaction concentration. The real-time fluorescence detection for isothermal nucleic acid amplification was performed at 65° C. for 30 minutes, and the amount of fluorescence was measured using CFX-96 (Bio-Rad, CA, USA) real-time fluorescence measurement equipment in every 1 minute.

FIG. 3 shows the results of LAMP isothermal nucleic acid amplification reaction using IB-DFO designed with FIP and RIP individually or together, wherein a similar fluorescence detection time was 16.02 min. 16.95 min and 16.40 min for $1\times10^4$ copies/reaction, respectively; 18.41 min, 18.65 min and 20.64 min, respectively for $1\times10^3$ copies/reaction in reactions containing EB_R_FIP_P2 or EB_R_RIP_P2 or using EB_R_FIP_P2 and EB_R_RIP_P2 together; and no fluorescence signal was detected for 0 copies/reaction with the addition of D.W. only. Therefore, the real-time fluorescence detection for a similar LAMP isothermal nucleic acid amplification was confirmed even when IB-DFO for FIP and RIP was used separately or together.

Example 4: Analysis of Fluorescence Detection Effect According to the Ratio of the Inner Primer Designed to the Same Sequence as the Oligonucleotide (IB-DFO) of the Present Invention In order to observe the fluorescence detection effect according to LAMP isothermal nucleic acid amplification reaction when the IB-DFO of the present invention and inner primer were designed with same sequences and used according to a ratio of them, four types of primers for LAMP isothermal nucleic acid amplification were designed by PrimerExplorer V4 Software on the L segment (Polymerase) site sequence of Bundibugyo, one of the subtypes of Ebola virus. The designed primers were EB_B_F3 (SEQ ID NO: 1), EB_B_R3 (SEQ ID NO: 2), EB_B_FIP (SEQ ID NO: 3) and EB_B_RIP (SEQ ID NO: 4); and IB-DFO used EB-B_FIP_P2 (SEQ ID NO: 5) obtained by replacing Thymine with internal dT on EB_B_FIP primer sequence, replacing FAM with the reporter dye on this site, replacing Thymine in 31 mer interval position with internal dT and attaching BHQ1 quencher on this site.

The isothermal nucleic acid amplification reaction for the IB-DFO oligonucleotides was performed by using 20 mM Tris-HCl (pH 8.8), 50 mM KCl, 10 mM MgSO4, 10 mM (NH4) 2SO4, 0.1% Tween-20, 1.4 mM dNTP each and 8 U Bst DNA polymerase (MCLAB, CA, USA) and 0.2 uM of each EB_B_F3 and EB_B_R3, and 1.6 Um of EB_B_RIP, and adding EB_B_FIP:EB_B_FIP_P2 in the ratios of 0:1.6 uM, 0.4:1.2 uM, 0.8:0.8 uM, 1.2:0.4 uM and 1.6:0 uM to the mixture, respectively. Bundibugyo L segment (gb: FJ217161, 521 bp) of Ebola virus was constructed through gene synthesis and then used in the concentration of $1\times10^7$ copies/reaction concentration. Real-time fluorescence detection for isothermal nucleic acid amplification was performed at 65° C. for 60 minutes, and the amount of fluorescence was measured using CFX-96 (Bio-Rad, CA, USA) real-time fluorescence measurement equipment in every 1 minute. And, an end-point fluorescence detection was performed at 65° C. for 60 minutes, and at 30° C. in every 1 minute for 10 cycles to determine the amount of fluorescence.

The results of FIGS. 3 and 4 show that the inner primer: IB-DFO was in the ratio of 0:1.6 uM and, from the results, fluorescence detection time was identified as being similar in the condition in which the inner primer was added, without use of the inner primer, and it was observed the result that RFU was decreased as the concentration of IB-DFO was decreased.

FIG. 4 shows the real-time fluorescence detection result, and FIG. 5 shows the end-point fluorescence detection result, and from the result, it was confirmed the same mode that as the concentration of the IB-DFO was reduced, RFU was reduced. Therefore, it was identified that IB-DFO performed two functions together as the primer and probe, and had an advantage that it can perform the real-time fluorescence detection and end-point fluorescence detection.

Example 5: Analysis of the Effect for LAMP Isothermal Nucleic Acid Amplification Detection with Plasmid DNA as a Template by Applying the Oligonucleotide (IB-DFO) of the Present Invention In order to observe the fluorescence detection effect according to LAMP isothermal nucleic acid amplification reaction with plasmid DNA as a template when adding the IB-DFO of the present invention to FIP position, six types of primers for LAMP isothermal nucleic acid amplification were designed by PrimerExplorer V4 Software on the L segment (Polymerase) site sequence of Bundibugyo, one of the subtypes of Ebola virus. The designed primers were EB_B_F3 (SEQ ID NO: 1), EB_B_R3 (SEQ ID NO: 2), EB_B_FIP (SEQ ID NO: 3), EB_B_RIP (SEQ ID NO: 4), EB_BLP_F (SEQ ID NO: 17) and EB_B_LP_R (SEQ ID NO: 18); and IB-DFO used EB-B_FIP_P2 (SEQ ID NO: 5) obtained by replacing Thymine with internal dT on EB_B_FIP primer sequence, replacing FAM with the reporter dye on this site, replacing Thymine in 33 mer interval position with internal dT and attaching BHQ1 quencher on this site.

The isothermal nucleic acid amplification reaction for the IB-DFO oligonucleotides was performed by using 20 mM Tris-HCl (pH 8.8), 50 mM KCl, 10 mM MgSO4, 10 mM (NH4) 2SO4, 0.1% Tween-20, 1.4 mM dNTP each, 8 U Bst DNA polymerase (MCLAB, CA, USA), 0.2 uM of each EB_B_F3 and EB_B_R3, and 0.8 uM of EB_B_LP_F and EB_B_LP_R; and adding 1.2 uM of EB_B_FIP and 1.6 uM of EB_R_RIP to the mixture; and adding 0.4 uM of EB_B_FIP_P2, IB-DFO of the present invention to the mixture. Bundibugyo L segment (gb:FJ217161, 521 bp) of Ebola virus was constructed through a gene synthesis and then used in the concentration of $1\times10^7$, $1\times10^6$, $1\times10^5$, $1\times10^4$, $1\times10^3$, $1\times10^2$, $1\times10^1$, 0 copies/reaction. The real-time fluorescence detection for isothermal nucleic acid amplification was performed at 65° C. for 60 minutes, and the amount of fluorescence was measured using CFX-96 (Bio-Rad, CA. USA) real-time fluorescence measurement equipment in every 1 minute. And, end-point fluorescence detection was performed at 65° C. for 60 minutes, and at 30° C. in every 1 minute for 10 cycles to determine the amount of fluorescence.

FIG. 6 shows the results determining the sensitivity for plasmid DNA in the range of the low concentration by real-time fluorescence detection with IB-DFO, and from the results, the positive detection was identified in $1\times10^7\sim1\times10^2$ copies/reaction, and the negative detection was identified in $1\times10^1$ and 0 copies/reaction. It was observed that the fluorescence detection time was 6.29 min, 8.01 min, 9.12 min, 10.12 min, 11.73 min and 13.17 min, respectively, from the high concentration.

FIG. 7 shows the result determining the end-point fluorescence detection, and the positive detection was confirmed in $1\times10^7\sim1\times10^2$ copies/reaction, and the negative detection was confirmed in $1\times10^1$ and 0 copies/reaction.

From the results of FIGS. 6 and 7, it could be confirmed whether the real-time and end-point fluorescence detections were detected equally according to the concentration of the template when using IB-DFO of the present invention, and the time for LAMP nucleic acid amplification reaction could be shortened when using the real-time fluorescence detection method.

Example 6: Analysis for the Effect of RT-LAMP Isothermal Nucleic Acid Amplification Detection with RNA Transcript as a Template by Applying the Oligonucleotide (IB-DFO) of the Present Invention In order to observe the fluorescence detection effect according to RT-LAMP isothermal nucleic acid amplification reaction with RNA transcript as a template when adding the IB-DFO of the present invention to FIP position, six types of primers for RT-LAMP isothermal nucleic acid amplification were designed by PrimerExplorer V4 Software on the L segment (Polymerase) site sequence of Bundibugyo, one of the subtypes of Ebola virus. The designed primers were EB_B_F3 (SEQ ID NO: 1), EB_B_R3 (SEQ ID NO: 2), EB_B_FIP (SEQ ID NO: 3), EB_B_RIP (SEQ ID NO: 4), EB_BLP_F (SEQ ID NO: 17) and EB_B_LP_R(SEQ ID NO: 18); and IB-DFO used EB-B_FIP_P2.5 (SEQ ID NO: 6) obtained by replacing Thymine with internal dT on EB_B_FIP primer sequence, replacing FAM with the reporter dye on this site, replacing Thymine in 25 mer interval position with internal dT and attaching BHQ1 quencher on this site.

The isothermal nucleic acid amplification reaction for the IB-DFO oligonucleotides was performed by using 20 mM Tris-HCl (pH 8.8), 50 mM KCl, 10 mM MgSO4, 10 mM (NH4) 2SO4, 0.1% Tween-20, 5 mM DTT, 5 U RNase inhibitor (New England Biolabs, MA, USA), 1.4 mM dNTP each, 8 U Bst DNA polymerase (MCLAB, CA, USA), 0.2 uM of EB_B_F3 and EB_B_R3, and 0.8 uM of EB_B_LP_F and EB_B_LP_R; adding 1.4 uM of EB_B_FIP and 1.6 uM of EB_R_RIP to the mixture and adding 0.2 uM of EB_B_FIP_P2.5, IB-DFO of the present invention to the mixture. Bundibugyo L segment (gb:FJ217161, 521 bp) of Ebola virus was constructed as the plasmid DNA through gene synthesis and then RNA transcript was synthesized using MEGAscript T7 Transcription Kit (Applied Biosystems, CA, USA) with the plasmid DNA through in vitro transcription. Bundibugyo RNA transcript was used in the concentration of $1\times10^5$, $1\times10^4$, $1\times10^3$ and 0 copies/reaction. The real-time fluorescence detection for isothermal nucleic acid amplification was performed at 65° C. for 30 minutes, and the amount of fluorescence was measured using CFX-96 (Bio-Rad, CA, USA) real-time fluorescence measurement equipment in every 1 minute. And, end-point fluorescence detection was performed at 65° C. for 60 minutes, and at 30° C. in every 1 minute for 10 cycles to determine the amount of fluorescence.

FIG. 8 shows the result determining RT-LAMP isothermal nucleic acid amplification real-time fluorescence, and the positive detection was confirmed up to $1\times10^5 \sim 1\times10^3$ copies/reaction, and the negative detection was confirmed at 0 copies/reaction using D.W. And, the fluorescence detection time was determined as being 8.72 min, 10.03 min and 10.98 min, respectively from the high concentration.

FIG. 9 shows the result determining the end-point fluorescence detection, and the positive detection was confirmed in $1\times10^5 \sim 1\times10^3$ copies/reaction similar to the result determining the real-time fluorescence detection, and the negative detection was confirmed at 0 copies/reaction using D.W.

From the results of FIGS. 8 and 9, it could be confirmed whether the real-time and end-point fluorescence detections were detected equally according to the concentration of the template in one-step RT-LAMP reaction using IB-DFO of the present invention, and when the real-time fluorescence detection method was used, the one-step RT-LAMP nucleic acid amplification reaction could shortened the reaction time like LAMP using DNA.

Example 7: Analysis for the Effect of LAMP Isothermal Nucleic Acid Amplification Detection with Plasmid DNA as the Template by Applying an Anti-Sense Probe Including the Quencher, as Designed by the Oligonucleotide (IB-DFO) of the Present Invention and by Temperature (55, 60, 65 and 70° C.)

An anti-sense probe was designed by adding IB-DFO of the present invention to FIP position, and designing the complementary anti-sense sequence from the reporter dye sequence of IB-DFO to 3' end according to the temperature (55, 60, 65 and 70° C.) to position the quencher on 3' end of the anti-sense sequence. Then, DB-DFO was added to RIP position and the anti-sense probe was designed at 60° C. In order to observe the real-time fluorescence detection effect of the anti-sense probe according to the design by the temperature in LAMP isothermal nucleic acid amplification reaction with the plasmid DNA as the template by using it, six types of primers for LAMP isothermal nucleic acid amplification were designed by PrimerExplorer V4 Software on the L segment (Polymerase) site sequence of Bundibugyo, one of the subtypes of Ebola virus. The designed primers were EB_B_F3 (SEQ ID NO: 1), EB_B_R3 (SEQ ID NO: 2), EB_B_FIP (SEQ ID NO: 3), EB_B_RIP (SEQ ID NO: 4), EB_BLP_F (SEQ ID NO: 17) and EB_B_LP_R(SEQ ID NO: 18); and IB-DFO used EB-B_FIP_P2 (SEQ ID NO: 5) obtained by replacing Thymine with internal dT on EB_B_FIP primer sequence, replacing FAM with the reporter dye on this site, replacing Thymine in 25 mer interval position with internal dT and attaching BHQ1 quencher on this site. The anti-sense probe used EB_B_FIP_P2_Q2_55 (SEQ ID NO: 19) designed at 55° C., EB_B_FIP_P2_Q2_60 (SEQ ID NO: 20) designed at 60° C., EB_B_FIP_P2_Q2_65 (SEQ ID NO: 21) designed at 65 t and EB_B_FIP_P2_Q2_70 (SEQ ID NO: 22) designed at 70° C. And, EB_B_RIP_P2_Q60 (SEQ ID NO: 23) obtained by designing the anti-sense probe complementary to IB-DFO of EB_B_RIP_P2 (SEQ ID NO: 8) at 60° C. was used.

The isothermal nucleic acid amplification reaction for the IB-DFO oligonucleotides was performed by using 20 mM Tris-HCl (pH 8.8), 10 mM KCl, 8 mM MgSO4, 10 mM (NH4) 2SO4, 0.1% Tween-20, 1.4 mM dNTP each, 8 U Bst DNA polymerase (MCLAB, CA, USA), 0.2 uM of EB_B_F3 and EB_B_R3, and 0.4 uM of EB_B_LP_F and EB_B_LP_R; and adding 1.2 uM of EB_B_FIP and 1.6 uM of EB_R_RIP to the mixture; and the mixture was prepared using 0.4 uM of EB_B_FIP_P2, IB-DFO of the present invention and 1.6 uM of the anti-sense probe, together with each of EB_B_FIP_P2_Q2_55, EB_B_FIP_P2_Q2_60, EB_B_FIP_P2_Q2_65, EB_B_FIP_P2_Q2_70. Then, IB-DFO was replaced with 0.4 uM of EB_B_RIP_P2, 1.6 uM of EB_B_RIP_P2_Q_60, the anti-sense probe for it was mixed, IB-DFO was mixed with EB_B_FIP_P2, each 0.4 uM of EB_B_RIP_P2 was mixed with 1.6 uM of EB_B_FIP_P2_Q2_60, and EB_B_RIP_P2_Q_60. Bundibugyo L segment (gb:FJ217161, 521 bp) of Ebola virus was constructed through gene synthesis and plasmid DNA was used in the concentration of $1\times10^5$, $1\times10^4$ and $1\times10^3$ copies/reaction. The real-time fluorescence detection for isothermal nucleic acid amplification reaction was performed at 65° C. for 60 minutes, and the amount of fluorescence was measured using AB7500 (Applied Biosystems, CA, USA) real-time fluorescence measurement equipment in every 1 minute.

FIGS. 10 and 13 show the result performing LAMP isotherm nucleic acid amplification real-time fluorescence measurement by designing the anti-sense probe according to the temperature and using it together with IB-DFO, and the fluorescence detection time observed in 1×10^5~1×10^3 copies/reaction at 55° C. was 13.4 min, 15.3 min and 18.4 min from the high concentration, respectively. The fluorescence was detected at 20.3 min, 22.7 min and 24.6 min, respectively at 60° C., and at 47.7 min and 49.7 min, respectively at 65° C., and no fluorescence was detected in 1×10^3 copies/reaction. No fluorescence was detected in all copes/reaction at 70° C. The amount of fluorescence was about 50% at 50° C. in relation to the anti-sense probe at 60° C., but the detection time was exhibited as being more faster about 6~7 minutes.

As a result of RN vs Min (non-normalization) type, as in FIG. 14, the background Rn of anti-sense probe at 55° C. was shown as being two times higher than that of the anti-sense probe at 60° C. As such, the background Rn and delta Rn can be regulated according to the design temperature of the anti-sense probe.

FIGS. 15 to 17 show the case that IB-DFO used FIP, RIP, or both of FIP and RIP, respectively, and the reaction was performed by including the anti-sense probe for it at 60° C., the amount of fluorescence was similar when each FIP and RIP was replaced, but IB-DFO of RIP was exhibited as being about 10 min faster than that of IB-DFO of FIP.

Sequence listing

SEQ ID NO: 1:EB_B_F3
5'-GTGTGTTCAAGTACAGCATT-3'

SEQ ID NO: 2:EB_B_R3
5'-ATAAGGGAGGATGATCAAGG-3'

SEQ ID NO: 3:EB_B_FIP
5'-ACCTGGTGTTAGATGTTTATCTGAGGCCAAACATTATTTTGATAGCC-3'

SEQ ID NO: 4:EB_B_RIP
5'-TACATTAAGAGGAACCAATTTCCGCTGATAGAATTCCCACAATAAGTCTT-3'

SEQ ID NO: 5:EB_B_FIP_P2
5'-ACCTGG(internal dT-FAM)GTTAGATGTTTATCTGAGGCCAAACATTATTT(internal dT-BHQ1)GATAGCC-3'

SEQ ID NO: 6:EB_B_FIP_P2.5
5'-ACCTGGTGT(internal dT-FAM)AGATGTTTATCTGAGGCCAAACAT(internal dT-BHQ1)ATTTTGATAGCC-3'

Sequence listing -continued

SEQ ID NO: 7:EB_B_FIP_P3
5'-ACCTGGTGTTAGA(internal dT-FAM)GTTTATCTGAGGCCAAACAT(internal dT-BHQ1)ATTTTGATAGCC-3'

SEQ ID NO: 8:EB_B_RIP_P2
5'-TACA(internal dT-FAM)TAAGAGGAACCAATTTCCGCTGATAGAAT(internal dT-BHQ1)CCCACAATAAGTCTT-3'

SEQ ID NO: 9:EB_R_F3
5'-GCCTCACAATGTTAATCTTAGC-3'

SEQ ID NO: 10:EB_R_R3
5'-GATTGTCTCCCATGACCG-3'

SEQ ID NO: 11:EB_R_FIP
5'-CCTCTATGCCTCCTAAGTGCCAATCGAGAATATCCTCCTGAA-3'

SEQ ID NO: 12:EB_R_RIP
5'-GATTACAACAAAAACTGTGGACGAGCTGATCGTAACTTAAAACCAGT-3'

SEQ ID NO: 13:Res_LP
5'-GGTACGAACTCGGGC-3'

SEQ ID NO: 14:Res_RLP
5'-TGTGCACAAATCTCCTTAGT-3'

SEQ ID NO: 15:EB_R_FIP_P2
5'-CCTC(internal dT-FAM)ATGCCTCCTAAGTGCCAATCGAGAATATCC(internal dT-BHQ1)CCTGAA-3'

SEQ ID NO: 16:EB_R_RIP_P2
5'-GAT(internal dT-FAM)ACAACAAAAACTGTGGACGAGCTGATCGTA AC(internal dT-BHQ1)TAAAACCAGT-3'

SEQ ID NO: 17:EB_B_LP_F
5'-ATTACACTATACCATGACCCTT-3'

SEQ ID NO: 18:EB_B_LP_R
5'-CACTGCCTATGATTAAAGACT-3'

SEQ ID NO: 19:EB_B_FIP_P2-Q2_55
5'-CCTCAGATAAACATCTAAC-BHQ1-3'

SEQ ID NO: 20:EB_B_FIP_P2-Q2_60
5'-GGCCTCAGATAAACATCTAAC-BHQ1-3'

SEQ ID NO: 21:EB_B_FIP_P2-Q2_65
5'-TGTTTGGCCTCAGATAAACATCTAAC-BHQ1-3'

SEQ ID NO: 22:EB_B_FIP_P2-Q2_70
5'-GGCTATCAAAATAATGTTTGGCCTCAGATAAACATCTAAC-BHQ1-3'

SEQ ID NO: 23:EB_B_RIP_P2-Q_60
5'-CGGAAATTGGTTCCTCTTA-BHQ1-3'

---

The invention claimed is:

1. An oligonucleotide for use in a loop-mediated isothermal nucleic acid amplification (LAMP) reaction for a specific sequence of a target gene, characterized in that the oligonucleotide is one of oligonucleotides set forth in
- SEQ ID NO: 5: EB B FIP P2 5'-ACCTGG (internal dT-6-carboxyfluorescein)GTTAGATGTTTATCT-GAGGCCAA ACATTATTT (internal dT-2-[N-(2-hydroxyethyl)-4-[[2-methoxy-5-methyl-4-[(4-methyl-2-nitrophenyl)diazenyl]phenyl]diazenyl]anilino]ethanol) GATAGCC-3',
- SEQ ID NO: 6: EB B FIP P2.5 5'-ACCTGGTGT (internal dT-6-carboxyfluorescein)AGATGTTTATCTGAGGC-CAA ACAT (internal dT-2-[N-(2-hydroxyethyl)-4-[[2-methoxy-5-methyl-4-[(4-methyl-2-nitrophenyl)diazenyl]phenyl]diazenyl]anilino]ethanol) ATTTTGATAGCC-3',
- SEQ ID NO: 7: EB B FIP P3 5'-ACCTGGTGTTAGA (internal dT-6-carboxyfluorescein)GTTTATCT-GAGGCCAA ACAT (internal dT-2-[N-(2-hydroxyethyl)-4-[[2-methoxy-5-methyl-4-[(4-methyl-2-nitrophenyl)diazenyl]phenyl]diazenyl]anilino]ethanol) ATTTTGATAGCC-3',
- SEQ ID NO: 8: EB B RIP P2 5-TACA (internal dT-6-carboxyfluorescein)TAAGAGGAACCAAT-TTCCGCTGATA GAAT (internal dT-2-[N-(2-hydroxyethyl)-4-[[2-methoxy-5-methyl-4-[(4-methyl-2-nitrophenyl)diazenyl]phenyl]diazenyl]anilino]ethanol) CCCACAATAAGTCTT-3',
- SEQ ID NO: 15: EB R FIP P2 5'-CCTC (internal dT-6-carboxyfluorescein)ATGCCTCCTAAGTGC-CAATCGAGAA TATCC (internal dT-dT-2-[N-(2-hydroxyethyl)-4-[[2-methoxy-5-methyl-4-[(4-methyl-2-nitrophenyl)diazenyl]phenyl]diazenyl]anilino]ethanol) CCTGAA-3', or
- SEQ ID NO: 16: EB R RIP P2 5'-GAT(dT-6-carboxyfluorescein)ACAACAAAAACTGTGGACGAGCTGAT CGTA AC (internal dT-2-[N-(2-hydroxyethyl)-4-[[2-methoxy-5-methyl-4-[(4-methyl-2-nitrophenyl)diazenyl]phenyl]diazenyl]anilino]ethanol) TAAAACCAGT-3.

2. A kit for amplifying a certain gene for a specimen including the oligonucleotide according to claim 1, characterized in that the kit comprises the oligonucleotides set forth in SEQ ID NOS: 5-8 or SEQ ID NOS:15-16.

* * * * *

SEQUENCE LISTING

<160> NUMBER OF SEQ ID NOS: 23

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1

-continued gtgtgttcaa gtacagcatt                                              20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
ataagggagg atgatcaagg                                              20

<210> SEQ ID NO 3
<211> LENGTH: 47
<212> TYPE: DNA
<213> ORGANISM: Artificial Sequence
<220> FEATURE:
<223> OTHER INFORMATION: Oligonucleotide

<400> SEQUENCE: 3
acctggtgtt agatgtttat ctgaggccaa acattatttt gatagcc                47

<210> SEQ ID NO 4
<211> LENGTH: 50
<212> TYPE: DNA
<213> ORGANISM: Artificial Sequence
<220> FEATURE:
<223> OTHER INFORMATION: Oligonucleotide

<400> SEQUENCE: 4
tacattaaga ggaaccaatt tccgctgata gaattcccac aataagtctt             50

<210> SEQ ID NO 5
<211> LENGTH: 47
<212> TYPE: DNA
<213> ORGANISM: Artificial Sequence
<220> FEATURE:
<223> OTHER INFORMATION: Oligonucleotide
<220> FEATURE:
<221> NAME/KEY: mutation
<222> LOCATION: (7)
<223> OTHER INFORMATION: n=Amino-C6(or C2)-deoxythymine
<220> FEATURE:
<221> NAME/KEY: mutation
<222> LOCATION: (40)
<223> OTHER INFORMATION: n=Amino-C6(or C2)-deoxythymine

<400> SEQUENCE: 5
acctggngtt agatgtttat ctgaggccaa acattatttn gatagcc                47

<210> SEQ ID NO 6
<211> LENGTH: 47
<212> TYPE: DNA
<213> ORGANISM: Artificial Sequence
<220> FEATURE:
<223> OTHER INFORMATION: Oligonucleotide
<220> FEATURE:
<221> NAME/KEY: mutation
<222> LOCATION: (10)
<223> OTHER INFORMATION: n=Amino-C6(or C2)-deoxythymine
<220> FEATURE:
<221> NAME/KEY: mutation
<222> LOCATION: (35)
<223> OTHER INFORMATION: n=Amino-C6(or C2)-deoxythymine

<400> SEQUENCE: 6
acctggtgtn agatgtttat ctgaggccaa acatnattt gatagcc                 47

```
<210> SEQ ID NO 7
<211> LENGTH: 47
<212> TYPE: DNA
<213> ORGANISM: Artificial Sequence
<220> FEATURE:
<223> OTHER INFORMATION: Oligonucleotide
<220> FEATURE:
<221> NAME/KEY: mutation
<222> LOCATION: (14)
<223> OTHER INFORMATION: n=Amino-C6(or C2)-deoxythymine
<220> FEATURE:
<221> NAME/KEY: mutation
<222> LOCATION: (35)
<223> OTHER INFORMATION: n=Amino-C6(or C2)-deoxythymine

<400> SEQUENCE: 7
acctggtgtt agangtttat ctgaggccaa acatnatttt gatagcc          47

<210> SEQ ID NO 8
<211> LENGTH: 50
<212> TYPE: DNA
<213> ORGANISM: Artificial Sequence
<220> FEATURE:
<223> OTHER INFORMATION: Oligonucleotide
<220> FEATURE:
<221> NAME/KEY: mutation
<222> LOCATION: (5)
<223> OTHER INFORMATION: n=Amino-C6(or C2)-deoxythymine
<220> FEATURE:
<221> NAME/KEY: mutation
<222> LOCATION: (35)
<223> OTHER INFORMATION: n=Amino-C6(or C2)-deoxythymine

<400> SEQUENCE: 8
tacantaaga ggaaccaatt tccgctgata gaatncccac aataagtctt          50

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide

<400> SEQUENCE: 9
gcctcacaat gttaatctta gc          22

<210> SEQ ID NO 10
<211> LENGTH: 18
<212> TYPE: DNA
<213> ORGANISM: Artificial Sequence
<220> FEATURE:
<223> OTHER INFORMATION: Oligonucleotide

<400> SEQUENCE: 10
gattgtctcc catgaccg          18

<210> SEQ ID NO 11
<211> LENGTH: 42
<212> TYPE: DNA
<213> ORGANISM: Artificial Sequence
<220> FEATURE:
<223> OTHER INFORMATION: Oligonucleotide

<400> SEQUENCE: 11
cctctatgcc tcctaagtgc caatcgagaa tatcctcctg aa          42

<210> SEQ ID NO 12
<211> LENGTH: 47
```

```
<212> TYPE: DNA
<213> ORGANISM: Artificial Sequence
<220> FEATURE:
<223> OTHER INFORMATION: Oligonucleotide

<400> SEQUENCE: 12
gattacaaca aaaactgtgg acgagctgat cgtaacttaa aaccagt          47

<210> SEQ ID NO 13
<211> LENGTH: 15
<212> TYPE: DNA
<213> ORGANISM: Artificial Sequence
<220> FEATURE:
<223> OTHER INFORMATION: Oligonucleotide

<400> SEQUENCE: 13
ggtacgaact cgggc                                             15

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide

<400> SEQUENCE: 14
tgtgcacaaa tctccttagt                                        20

<210> SEQ ID NO 15
<211> LENGTH: 42
<212> TYPE: DNA
<213> ORGANISM: Artificial Sequence
<220> FEATURE:
<223> OTHER INFORMATION: Oligonucleotide
<220> FEATURE:
<221> NAME/KEY: mutation
<222> LOCATION: (5)
<223> OTHER INFORMATION: n=Amino-C6(or C2)-deoxythymine
<220> FEATURE:
<221> NAME/KEY: mutation
<222> LOCATION: (36)
<223> OTHER INFORMATION: n=Amino-C6(or C2)-deoxythymine

<400> SEQUENCE: 15
cctcnatgcc tcctaagtgc caatcgagaa tatccncctg aa               42

<210> SEQ ID NO 16
<211> LENGTH: 47
<212> TYPE: DNA
<213> ORGANISM: Artificial Sequence
<220> FEATURE:
<223> OTHER INFORMATION: Oligonucleotide
<220> FEATURE:
<221> NAME/KEY: mutation
<222> LOCATION: (4)
<223> OTHER INFORMATION: n=Amino-C6(or C2)-deoxythymine
<220> FEATURE:
<221> NAME/KEY: mutation
<222> LOCATION: (37)
<223> OTHER INFORMATION: n=Amino-C6(or C2)-deoxythymine

<400> SEQUENCE: 16
gatnacaaca aaaactgtgg acgagctgat cgtaacntaa aaccagt          47

<210> SEQ ID NO 17
<211> LENGTH: 22
<212> TYPE: DNA
<213> ORGANISM: Artificial Sequence
<220> FEATURE:
```

```
<223> OTHER INFORMATION: Oligonucleotide

<400> SEQUENCE: 17
attacactat accatgaccc tt                                          22

<210> SEQ ID NO 18
<211> LENGTH: 21
<212> TYPE: DNA
<213> ORGANISM: Artificial Sequence
<220> FEATURE:
<223> OTHER INFORMATION: Oligonucleotide

<400> SEQUENCE: 18
cactgcctat gattaaagac t                                           21

<210> SEQ ID NO 19
<211> LENGTH: 19
<212> TYPE: DNA
<213> ORGANISM: Artificial Sequence
<220> FEATURE:
<223> OTHER INFORMATION: probe

<400> SEQUENCE: 19
cctcagataa acatctaac                                              19

<210> SEQ ID NO 20
<211> LENGTH: 21
<212> TYPE: DNA
<213> ORGANISM: Artificial Sequence
<220> FEATURE:
<223> OTHER INFORMATION: probe

<400> SEQUENCE: 20
ggcctcagat aaacatctaa c                                           21

<210> SEQ ID NO 21
<211> LENGTH: 26
<212> TYPE: DNA
<213> ORGANISM: Artificial Sequence
<220> FEATURE:
<223> OTHER INFORMATION: probe

<400> SEQUENCE: 21
tgtttggcct cagataaaca tctaac                                      26

<210> SEQ ID NO 22
<211> LENGTH: 40
<212> TYPE: DNA
<213> ORGANISM: Artificial Sequence
<220> FEATURE:
<223> OTHER INFORMATION: probe

<400> SEQUENCE: 22
ggctatcaaa ataatgtttg gcctcagata aacatctaac                       40

<210> SEQ ID NO 23
<211> LENGTH: 19
<212> TYPE: DNA
<213> ORGANISM: Artificial Sequence
<220> FEATURE:
<223> OTHER INFORMATION: probe

<400> SEQUENCE: 23
cggaaattgg ttcctctta                                              19
```